(12) United States Patent
Ramage et al.

(10) Patent No.: US 6,359,113 B1
(45) Date of Patent: Mar. 19, 2002

(54) PROTECTIVE GROUP, COMPOUND PROTECTED BY SAID GROUP AND DEVICE FOR GRAFTING THE PROTECTIVE GROUP ON THE COMPOUND TO PROTECT IT

(75) Inventors: Robert Ramage, Edinburgh; Gilles Raphy, Herts, both of (GB)

(73) Assignee: Rhodia Chimie, Courbevoie (FR)

( * ) Notice: Subject to any disclaimer, the term of this patent is extended or adjusted under 35 U.S.C. 154(b) by 0 days.

(21) Appl. No.: 09/162,777

(22) Filed: Sep. 30, 1998

Related U.S. Application Data

(60) Division of application No. 08/288,771, filed on Aug. 11, 1994, now Pat. No. 5,869,605, which is a continuation of application No. 08/003,698, filed on Jan. 13, 1993, now abandoned, which is a continuation-in-part of application No. 07/920,579, filed as application No. PCT/FR91/01083 on Dec. 31, 1991, now abandoned.

(30) Foreign Application Priority Data

Dec. 31, 1990 (GB) .............................................. 9028208

(51) Int. Cl.$^7$ ................................................. C07K 1/06
(52) U.S. Cl. ...................... 530/335; 530/345; 530/344; 540/2; 552/200; 552/208; 210/198.2
(58) Field of Search ................................. 530/344, 335; 210/198.2; 540/2; 552/200, 208

(56) References Cited

U.S. PATENT DOCUMENTS

| | | | |
|---|---|---|---|
| 3,744,877 A | 7/1973 | Stamm | 350/160 P |
| 3,862,026 A | 1/1975 | Friend | 208/310 |
| 4,457,866 A | 7/1984 | Karges et al. | 260/112.5 |
| 4,631,119 A | 12/1986 | Gokel et al. | 204/59 |
| 4,666,862 A | 5/1987 | Chan | 436/501 |
| 4,677,193 A | 6/1987 | Rivier et al. | 530/313 |
| 4,737,454 A | 4/1988 | Dattagupta et al. | 435/6 |
| 4,766,110 A | 8/1988 | Ryan et al. | 514/19 |
| 4,777,128 A | 10/1988 | Lippa | 435/5 |
| 4,985,184 A | 1/1991 | Takahashi | 264/6 |
| 5,037,615 A | 8/1991 | Kane | 422/82.08 |
| 5,045,537 A | 9/1991 | Weidmann | 514/63 |
| 5,161,694 A | 11/1992 | Yoon | 209/5 |
| 5,175,273 A | 12/1992 | Bischofberger et al. | 536/27 |
| 5,254,477 A | 10/1993 | Walt | 436/172 |
| 5,370,794 A | 12/1994 | Obayashi | 210/198.2 |
| 5,788,865 A | 8/1998 | Smirnov | 210/690 |

OTHER PUBLICATIONS

Abstract of JP–252734, Nov. 4, 1987.*
Colin, J. Chromatog. 122, 223–242, 1976.
Ciccioli, J. Chromatog. 269, 47–60, 1983.
R. Schoental et al., "Fluorescence Spectra of Polycyclic Aromatic Hydrocarbons in Solution," J. Chem. Soc., (1949), pp. 1683–1696.
H.J. Creech et al., "The Conjugation of Horse Serum Albumin with Isocyanates of Certain Polynuclear Aromatic Hydrocarbons," J. Am. Chem. Soc., vol. 63, (Jun. 1941), pp. 1661–1669.
E.G. Rogan et al., "Mutagenicity of Benzylic Acetates, Sulfates and Bromides of Polycyclic Aromatic Hydrocarbons," Chem.–Biol. Interactions, vol. 58 (1986), pp. 253–275.
W. Carruthers, "Some Modern Methods of Organic Synthesis," 2$^{nd}$ Ed., pp. 395–396.
W. Lijinsky et al., "Fluorescence Spectra of 59 Polycyclic Aromatic Hydrocarbons," Chicago Medical School Quarterly, vol. 21, pp. 49–77.
G.M. Edelman et al., "Fluorescent Probes and the Conformation of Proteins," Accounts of Chemical Research, vol. 1, No. 3, (Mar. 1968) pp. 65–70.
L. Brand et al., "Fluorescence Probes for Structure," Annual Review of Biochemistry, vol. 41, (1972) pp. 843–868.
T.H. Lowry et al., "Mechanism and Theory in Organic Chemistry," Harper & Row, (1976), pp. 681–683.
E.J. Bowen et al., "The Fluorescence Spectra of Coronene and 1:12–Benzoperylene at Low Temperatures," J. Chem. Soc. (1954), pp. 3875–3878.

* cited by examiner

*Primary Examiner*—Christopher S. F. Low
*Assistant Examiner*—David Lukton
(74) *Attorney, Agent, or Firm*—Finnegan, Henderson, Farabow, Garrett & Dunner, L.L.P.

(57) ABSTRACT

The protective group having the following formula (I):

$$Ar—L— \qquad (I)$$

wherein
  Ar represents a substantially planar, fused ring system containing at least 4 aromatic rings, and
  L represents a group containing at least one carbon atom which is capable of bonding to a group to be protected.

15 Claims, 2 Drawing Sheets

```
                         SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:1:

Gly Ser Met Val Leu Ser
             5

(2) INFORMATION FOR SEQ ID NO:2:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:2:

Ser Met Val Leu Ser
1               5

(2) INFORMATION FOR SEQ ID NO:3:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:3:
```

```
Gly Arg Thr Leu Ser Asp Tyr Asn Ile Gln Lys Glu Ser Thr Leu His
1               5                   10                  15

Leu Val Leu Arg Leu Arg Gly Gly
            20
```

(2) INFORMATION FOR SEQ ID NO:4:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:4:

```
Arg Thr Leu Ser Asp Tyr Asn Ile Gln Lys Glu Ser Thr Leu His Leu
1               5                   10                  15

Val Leu Arg Leu Arg Gly Gly
            20
```

(2) INFORMATION FOR SEQ ID NO:5:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Ile Pro Pro Asp Gln Gln Arg Leu Ile Phe Ala Gly Lys Gln Leu
1               5                   10                  15

Glu Asp Gly Arg Thr Leu Ser Asp Tyr Asn Ile Gln Lys Glu Ser Thr
                20                  25                  30

Leu His Leu Val Leu Arg Leu Arg Gly Gly
            35                  40
```

(2) INFORMATION FOR SEQ ID NO:6:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:6:

```
Ile Pro Pro Asp Gln Gln Arg Leu Ile Phe Ala Gly Lys Gln Leu Glu
1               5                   10                  15

Asp Gly Arg Thr Leu Ser Asp Tyr Asn Ile Gln Lys Glu Ser Thr Leu
                20                  25                  30

His Leu Val Leu Arg Leu Arg Gly Gly
            35                  40
```

(2) INFORMATION FOR SEQ ID NO:7:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:7:

```
Pro Pro Asp Gln Gln Arg Leu Ile Phe Ala Gly Lys Gln Leu Glu Asp
```

-continued

```
              1               5              10              15
        Gly Arg Thr Leu Ser Asp Tyr Asn Ile Gln Lys Glu Ser Thr Leu His
                             20                  25              30
        Leu Val Leu Arg Leu Arg Gly Gly
                        35              40
```

PROTECTIVE GROUP, COMPOUND PROTECTED BY SAID GROUP AND DEVICE FOR GRAFTING THE PROTECTIVE GROUP ON THE COMPOUND TO PROTECT IT

This is a division of application Ser. No. 08/288,771, filed Aug. 11, 1994 now U.S. Pat. No. 5,869,605, which is a continuation of application Ser. No. 08/003,698, filed Jan. 13, 1993, abandoned, which is a continuation-in-part of application Ser. No. 07/920,579, filed Oct. 30, 1992, abandoned, which is a 371 of PCT/FR91/01883 filed Dec. 31, 1991.

BACKGROUND OF THE INVENTION

In organic synthesis, in particular multistep synthesis, the purification of the products obtained can present more problems than the synthesis itself. This is particularly true in the case of peptide synthesis, a synthesis which systematically uses protective groups which can also play supplementary roles.

Thus, the need to protect, or activate, a certain function in amino acids has been used for carrying out biphasic peptide syntheses in order to facilitate the purification steps. Implicit in these techniques, such as the Merrifield technique (*J. Amer. Chem. Soc.*, 108, 5242 (1986)), however, is the problem of purification of the synthesized peptides which has not been completely resolved. One of the most elegant solutions to this problem would be to modify the peptide, or any other molecule requiring protection, by binding it to a solid in a manner which is physically reversible, both in the course of working up and purification. To date no protective group has been disclosed as being capable of exercising such a property.

It is for this reason that one of the main aims of the present invention is to provide a protective group corresponding to the above criteria.

SUMMARY OF THE INVENTION

Figure 1:
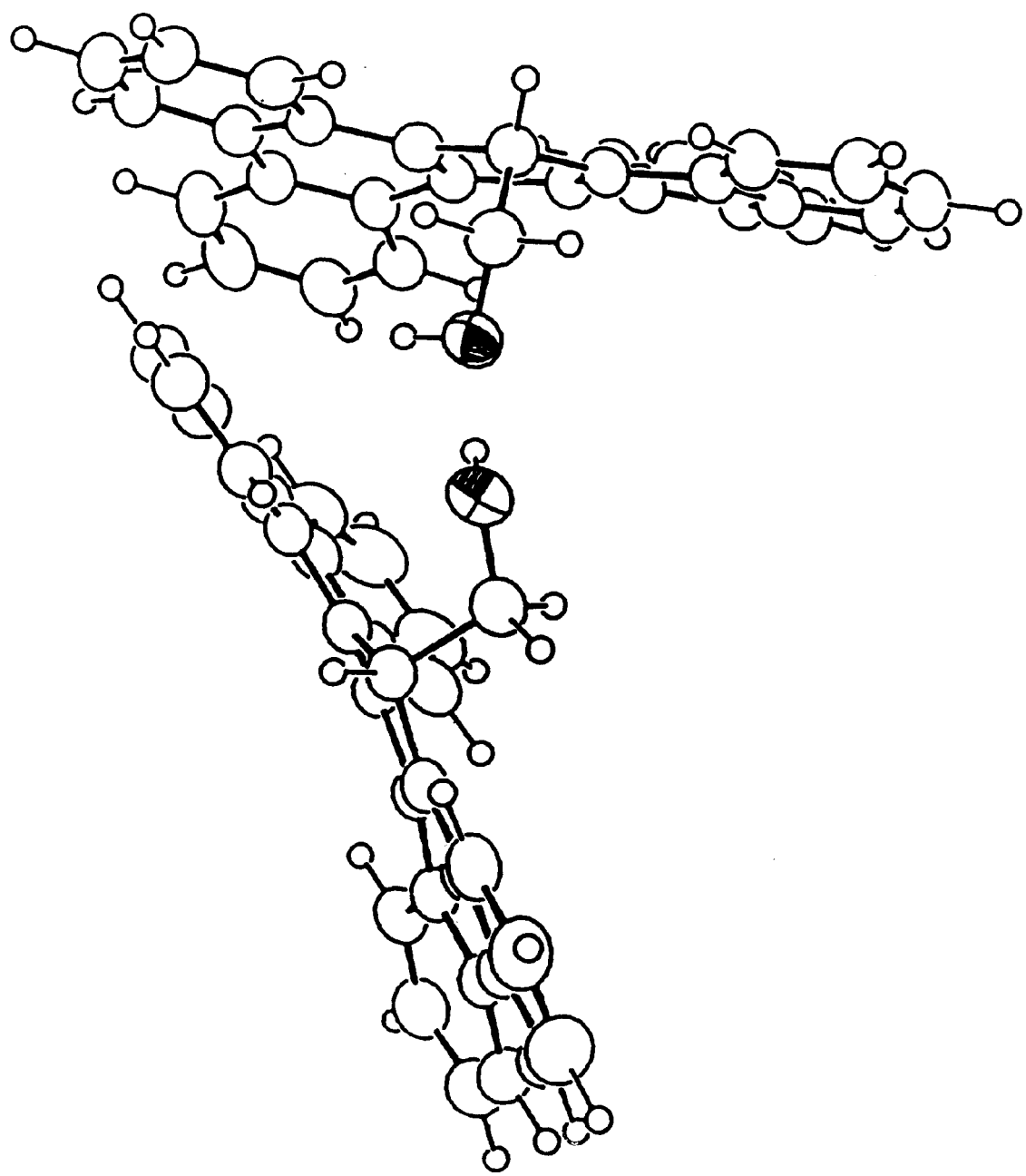
FIGS. 1 and 2 show the X-ray crystal structure of compound (31) of the present invention, 17-hydroxymethyltetrabenzo-(a,c,g,i)fluorene (Tbfmoc), as described in the Examples.

The present invention relates to a new protective group and its use, in particular, in peptide synthesis. It relates more particularly to a protective group facilitating the purification of compounds, especially peptides, during or at the end of a synthesis.

In a first embodiment, the present invention is directed to a protective group having the formula (I):

   (I)

wherein
Ar represents a substantially planar fused ring system containing at least 4 aromatic rings, and
L represents a group containing at least one carbon atom, which is capable of bonding to a group to be protected.
In a second embodiment, the present invention is directed to a protected compound comprising a protective group as described above attached to a group of a compound to be protected.

In a third embodiment, the present invention is directed to a fluorescent label having the formula:

   (I)

wherein
Ar represents a substantially planar fused ring system containing at least 4 aromatic rings; and
L represents a group containing at least one carbon atom which is capable of bonding to a group to be labelled.
The present invention is further directed to a device, which comprises
a) a chamber filled with a graphite material, and
b) a kit for grafting a protective group as described above onto a molecule.

Additionally, the present invention is directed to a process for the synthesis or separation of a mixture of compounds, comprising the steps of:
a) protecting at least one group in at least one compound in a mixture of compounds to be separated with a protective group as described above, and
b) passing the mixture of compounds through a chamber filled with a graphite material.

DETAILED DESCRIPTION OF THE PREFERRED EMBODIMENTS

The present invention provides a protective group having the following formula (I):

   (I)

wherein
Ar represents a substantially planar fused ring system containing at least 4 aromatic rings, and
L represents a group containing at least one carbon atom, which is capable of bonding to a group to be protected.
Protective groups of this type are disclosed in R. Ramage et al., *Tetrahedron Letters,* 33(3), 385–388 (1992), which is herein incorporated by reference.

The Ar group preferably contains at least 6 aromatic rings and the aromatic rings are preferably hexagonal. Preferably, Ar does not contain a heteroatom.

The L group may be, for example, an alkyl group or, in particular, a peptide group. Generally, the L group may comprise any link, or branch, known to those skilled in the art for forming a link between the protective group and the molecule to be protected. The L group is generally selected such that there is no conjugation between the Ar group and the molecule to be protected.

The L group is preferably connected by a carbon atom to the Ar group. Particular preferred Ar—L— groups include those having the formulae (IA) to (IF):

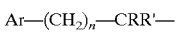   (IA)

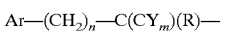   (IB)

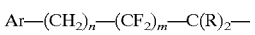   (IC)

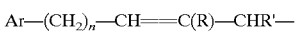   (ID)

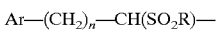   (IE)

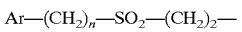   (IF)

wherein
R and R' are each hydrogen, alkyl, aryl, aralkyl or cycloalkyl;

Y is halogen, such as chlorine, bromine or iodine;

n is an integer of from 0 to 5; and m is an integer of from 1 to 8.

Particularly preferred Ar—L— groups that have the formula (IA) are those in which the total number of carbon atoms contained in the groups R and R' is no more than 15. More particularly preferred are those groups in which R is hydrogen, R' is aryl and n is 0.

Additionally, when the function to be protected is $NH_2$ or an alcohol, precursors of preferred Ar—L— groups include those having formulae (IG), (IH) and (IJ):

(IG)

(IH)

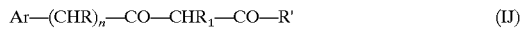
(IJ)

wherein

R, $R_1$ and R' are each hydrogen, alkyl, aryl, aralkyl or cycloalkyl, and n is an integer of from 0 to 5.

Preferred Ar—L— groups have the formula Ar—CHR—L', in which L' is a direct bond or a group capable of bonding to a group to be protected and R is a hydrogen atom or an alkyl group, preferably having up to 4 carbon atoms. Especially preferred groups of the present invention have the formula (II):

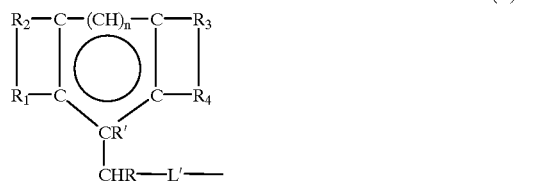
(II)

wherein n is an integer of 0 or 1;

O means that the surrounding ring is aromatic when n is 1 and non-aromatic when n is 0;

$R_1$ and $R_2$, on the one hand, and $R_3$ and $R_4$, on the other hand, are chosen so as each to form a fused aromatic ring system together with the carbon atoms to which they are attached;

R and R' are each an alkyl group or hydrogen, provided that when n is 1, R' is absent; and L' represents a direct bond or a group capable of bonding to a group to be protected. More particularly preferred Ar—L— groups are those in which R is hydrogen.

To rigidify the protective group, it is possible to provide a group $R_5$ to form one or more supplementary aromatic rings, the rings preferably being of hexagonal structure and advantageously not containing a heteroatom, to give a protective group of the formula (III):

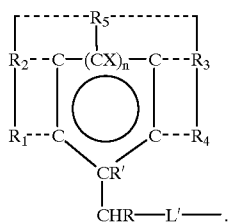

wherein X represents a bond to $R_5$ or a hydrogen atom. Additionally, when n is 0 there is no bond between the central ring and $R_5$ and when n is 1 the bond between one of $R_5$ and $R_2$ and $R_5$ and $R_3$ is optional but preferred.

The total number of aromatic rings is advantageously from 4 to 8. The free apexes may be substituted by alkyl groups, advantageously having a short chain (from 1 to 5 carbon atoms). The total number of carbon atoms in the group (not taking account of the link L) is generally from 20 to 60, preferably from 25 to 50, carbon atoms.

For ease of synthesis, $R_1$ and $R_2$, on the one hand, $R_3$ and $R_4$, on the other hand, and $R_5$ are advantageously chosen to form a system which is symmetrical relative to the central ring (relative to the bisector of the intra-ring angle of the carbon carrying the methylene attached to the link L'). The groups where n is 0, in particular those without radical $R_5$, are more readily accessible.

The chemistry of the groups according to the invention is the same as for group Fmoc when n is 0 and the same as for the benzyl group in the other cases, for example when n is 1. The chemistry of the group Fmoc is well known and reference may be made to the following articles as well as to the general publications on protective groups: Carpino, *J. Amer. Chem. Soc.* 92, 5748 (1970); *J. Org. Chem.* 37, 3404 (1972); *Synthesis*, p. 671 (1983); *F. Org. Chem.* 48, 77 (1983); *Int. J. Peptide Protein Res.* 22, 125 (1983); and *Biopolymers*, 22, 2157 (1983).

The above groups are easy to obtain by the following sequence of reactions or equivalents:

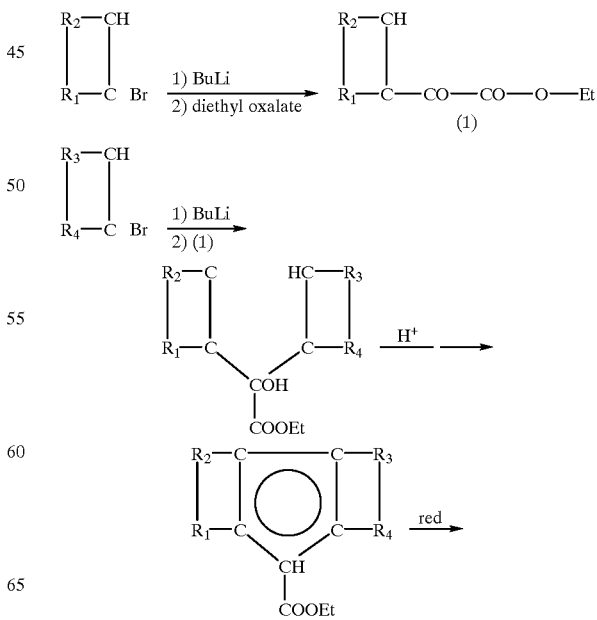

-continued

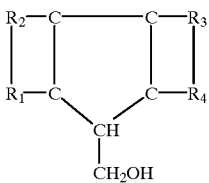

The chemistry of the benzyl group is also well-known and it is appropriate to refer to the teaching and specialized publications on the subject. Reference may also be made to the following articles which broke new ground: *Int. J. Peptide Protein Res.*, 27, 358 (1986); *Synthesis*, p. 303 (1986); *J. Org. Chem.*, 48, 661 and 666 (1983).

The groups of the present invention may be prepared by those methods described in the above articles and by well-known techniques, such as Freidel-Crafts reactions.

The above articles indicate to those skilled in the art how to graft the protective groups specified above to the functions to be protected. These groups thus may modify molecules having, for example, an acid, alcohol, thiol, amine or amide function. The molecules protected in this way can be molecules of any type. Preferably, molecules protected in this way are amino acids, peptides, nucleosides and nucleotides. The constituent amino acids of the peptides may be natural or obtained by synthesis. Peptides, amino acids, nucleosides and nucleotides may be protected or substituted on their various functions. Preferred functions to be protected include —O—P, —S—P, —O—CO—O—P, —O—CO—NA—P, —O—CO—P, —NA—CO—P, and $(-)_2$N—CO—P, in which A is hydrogen, alkyl, or aryl and P is the remainder of the molecule having the function to be protected.

Generally, the protective group of the present invention may be removed from the protected function by any of the methods known to those having skill in the art. For example, when the protective group has the formula (IA), the protective group may be removed by acidolysis. Similarly, when the protective group has the formula (IB) or (IC), the protective group may be removed by treatment with zinc and acetic acid. Likewise, when the protective group has the formula (ID), the protective group may be removed by treating the protected compound with a catalyst comprising a Group VIII element, such as palladium, complexed with a water-soluble coordinating agent in an aqueous phase. The protective group having the formula (ID) may also be removed by hydrogenation over a suitable catalyst.

The present invention also provides a protecting compound comprising a group as defined above attached, via the L or L' group, to a leaving group, such as a group which contains a nitrogen, oxygen, sulphur, selenium, tellurium, silicon or halogen atom. Examples of leaving groups are halogen atoms (e.g., F, Cl, Br or I), —OH, —COOH, —NH$_2$, —CONH$_2$, —SO$_3$C$_6$H$_4$—pCH$_3$, —SH, —CN or —Si(CH$_3$)$_3$ groups.

In any multi-step synthesis, it is important to select a protecting group that is both stable to reaction conditions and easily removed, when desired, to provide a final product. The protecting groups according to the present invention are particular suited for use in the multi-step synthesis of peptides and oligonucleotides, due to their stability to the reaction conditions normally employed in such syntheses and their easy removability at the end of the synthesis. Additionally, the lipophilic nature of the protecting group of the present invention enables the synthesis of peptides to occur in water-immiscible organic solvents.

It has also been shown, surprisingly, that molecules modified in accordance with the protective groups of the present invention are remarkably well-retained on graphite columns or on columns of graphitized materials, such as activated charcoal, and this adsorption is reversible. The strong affinity of the protective group of the present invention means that it is especially suitable for the purification of peptides. These modified molecules also present an equally good capacity for chiral separation.

The more aromatic rings carried by the group, the better is the adsorption and the more difficult the elution, and vice versa; the optimum being defined case by case by those skilled in the art. However, 4 to 8 aromatic rings, in addition to the central ring, constitute, in general, a satisfactory compromise both from the economic point of view and from the point of view of the adsorption and elution criteria.

It is expedient to include under the term graphitized materials those which are carbonaceous throughout or at the surface and have undergone a graphitization treatment, in general by pyrolysis. The use of activated charcoal provides equivalent binding as with graphite and is preferred, as activated charcoal is cheaper than graphitized carbon (PGC).

The groups according to the present invention are also absorbers of visible or ultraviolet radiation in wavelengths which differ from those for natural amino acids. Some of these groups fluoresce at wavelengths different from those of the natural amino acids. Accordingly, the groups according to the present invention may be used as fluorescent labels, attached to a molecule of interest via the L group. For example, 17-hydroxytetrabenzo-(a,c,g,i)fluorene (Tbfmoc) can act as a fluorescent label, having an excitation wavelength of 383 nm and an emission wavelength of 424 nm. This is particular advantageous in immunology, where detection of compounds present in very low concentrations requires highly sensitive techniques.

The Tbfmoc group is particularly suitable for biological applications, such as pharmacology and immunology, in part due to its lack of mutagenic activity. For example, the Tbfmoc group did not exhibit mutagenic activity in strains of *Salmonella typhimurium*, with and without metabolic activation.

The property of absorbance also enables devices to be developed comprising, for successive or simultaneous use:
a) a chamber, such as a column, filled with a graphite material, preferably graphite or activated charcoal, and
b) a kit for grafting a protective group as defined above on a molecule.

The graphite or graphitized material has been defined above, while the kit for grafting the protective group comprises the various reagents known to those skilled in the art for grafting a protective group on a molecule to be protected. This device is advantageously completed by (c) a fraction-collecting system fitted with an ultraviolet (UV), visible spectroscopic, or fluorescent spectroscopic detector.

Thus, it has been possible to develop a new process for synthesis and/or separation of molecules, in particular peptide fragments, which comprises the following steps:
protecting at least one group in at least one compound in a mixture of compounds to be separated with a group as defined above, and
passing the mixture of compounds through a chamber filled with a graphite material.

The present invention is now further illustrated in the following Examples:

All amino acid derivatives were purchased from either Fluka, Aldrich or Sigma. Melting points were taken in open capillaries on an electrically heated Buchi 510 melting point apparatus, or on microscope slides on an electrically heated Reichert 7905 hot stage and are uncorrected. Thin-layer chromatography (t.l.c.) was carried out using plastic sheets coated with silica gel 60 GF-254 (Merck 5735) in the following systems:

(A) ethyl acetate/petrol (b.p. 40–60° C.) (1:4)

(B) methanol/chloroform (1:9)

(C) toluene (D) chloroform (E) ethyl acetate (F) benzene (G) dichloromethane (H) methanol/chloroform/acetic acid (1:9:0.5)

(I) n-butanol/acetic acid/water (3:1:1)

Visualization of the compounds was achieved by a suitable combination of the following methods: iodine vapor, ultraviolet absorption at 254 nm or 352 nm, neutral potassium permanganate and bromophenol blue sprays, Mary's reagent (4,4'-bis(dimethylamino)diphenyl carbinol) for acid functions and ninhydrin for compounds with free amino groups. Optical rotations were measured on an AA 1000 polarimeter using a 1 dm cell in the solvents quoted in the text. High performance liquid chromatography (HPLC) was performed using either a Waters system, i.e., 2×600 A pumps, a U6K injector, a 680 automatic gradient controller, a model 441 ultraviolet detector; or an Applied Biosystems system, i.e., 2×1406 A solvent delivery system, a 1480 A injector/mixer, and a 1783 A detector/controller. Analytical separations were carried out on a Whatman Partisil-5 ODS-3 (4.6 mm ID×250 mm) and on a ABI (RP18) aquapore OD-300, 300 Å pore size, 7 μm spherical silica (4.6 mm ID×220 mm) column, under the conditions indicated in the text. Flash chromatography was performed using silica gel 60 (230–400 mesh (Fluka); 60–100 g of silica per gram of crude material; active length 15–20 cm). Infrared spectra were recorded on a Perkin Elmer 781 spectrophotometer in the solvent indicated or by the KBr disc technique, using polystyrene as the standard (1603 cm$^{-1}$). Ultraviolet spectra were recorded on a Cary 210 spectrophotometer and fluorescence spectra on a Perkin Elmer LS-5 luminescence spectrophotometer. Mass spectra were measured on a Kratos MS 50 TC machine. Proton nuclear magnetic resonance (NMR) spectra were recorded on either Bruker WP 80 (80 MHz), WP 200 (200 MHz) or WH 360 (360 MHz) machines in the solvent indicated, using external tetramethylsilane as the standard (δ=0.00). Carbon-13 NMR spectra were recorded on a Bruker WP 200 (50 MHz) or WH 360 (90 MHz) machines in the solvent indicated, using tetramethylsilane as the standard. Elemental analyses were carried out on a Carlo Erba model 1106 elemental analyzer. Single crystal X-ray structure determination was performed on a Stoe Stadi-4 four-circle diffractometer, graphite-monochromated (Cu-Kα radiation, λ=1.54184 Å). All solvents were distilled before use and the following were dried using the reagents given in parentheses when required: benzene (sodium wire), chloroform (phosphorus pentoxide), dichloromethane (calcium hydride), diethyl ether (sodium wire), dioxan (neutral alumina and sodium wire), methanol (magnesium-iodine), toluene (sodium wire). Petrol (b.p. 40–60° C.) refers to that fraction which boils between 40° C. and 60° C.

EXAMPLE 1
Synthesis of 13-hydroxymethyldibenzo(a,c)fluorene

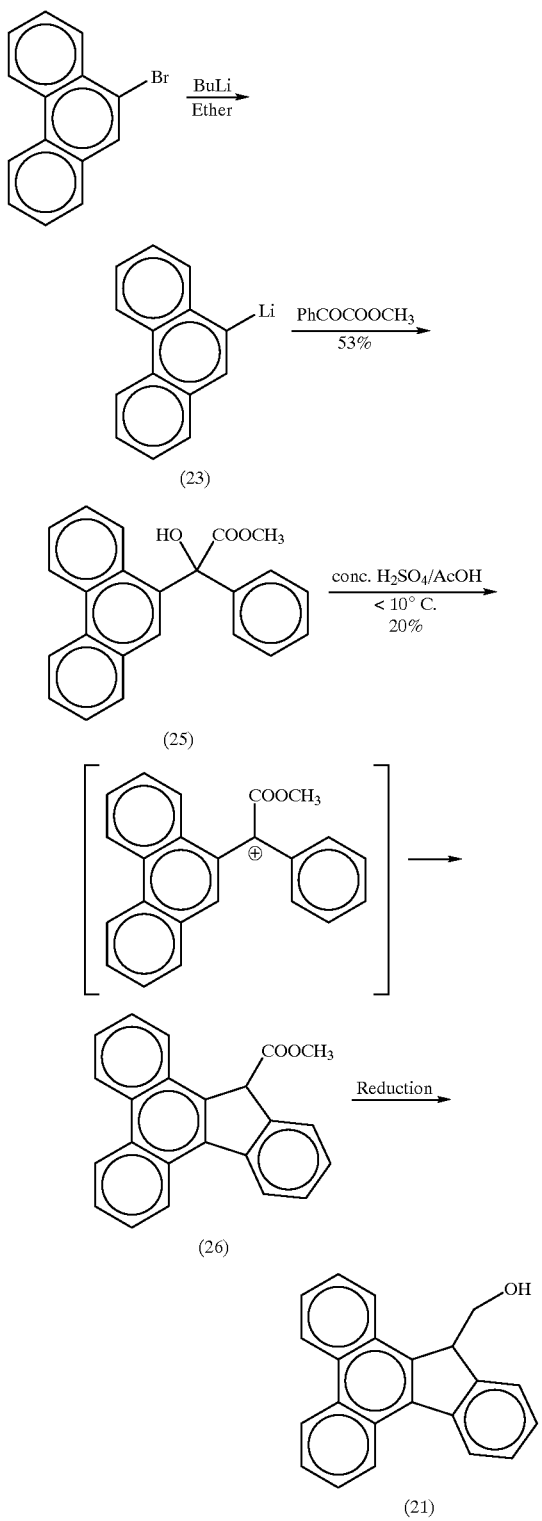

Methyl (phenanthren-9-yl, phenyl)hydroxyacetate (25)

The synthesis of methyl(phenanthren-9-yl, phenyl) hydroxyacetate (25) was carried out in ether by reaction of 9-phenanthrenyl lithium (23) with methyl benzoylformate.

To a cold (0° C.) solution of 9-bromophenanthrene (2.57 g, 10 mmol) in dry ether (10 ml) under nitrogen, was added a solution of n-butyllithium in hexane (8 ml, 11 mmol; 1.1 equiv; 1.38M titrated) dropwise over 10 min. The reaction mixture was stirred for one hour at room temperature. The resultant suspension was allowed to settle and then the supernatant removed by syringe. The residue was resuspended in ether (5 ml). This solution was added, under nitrogen, to a cold (0° C.) solution of methyl benzoylformate (1.64 g, 1.4 ml, 10 mmol) in 50 ml of diethylether. The resulting mixture was heated under reflux for 2 h and allowed to stir overnight. After addition of dilute (10% v/v) HCl (50 ml; pH=1), the organic layer was separated, combined with ether washings (2×50 ml) of the aqueous layer, washed with water (2×50 ml) and dried with $MgSO_4$. The solvent was removed under vacuum to give a yellow oil. After purification by flash chromatography (eluent: (A)), a yellow oil was obtained which was triturated with petrol. A white solid was obtained which was filtered and dried in a vacuum desiccator to give compound (25) (1.75 g, 51%); m.p. 143–145° C. (Found: C, 79.7; H, 5.24; $C_{23}H_{18}O_3$ requires: C, 80.7; H, 5.26%); t.l.c. $R_f$(A) 0.32; $R_f$(B) 0.76; $v_{max}$ $CH_2Cl_2$ 3690 (free OH), 3510 (H bonded OH), 3025 (CH stretching, aryl), 2960, 2880, 2860 (CH stretching, alkyl), 1730 (CO, ester), 1600, 1500 (aromatic rings), 1225, 1185, 1170, 1110, 1100, 1070 (CO stretching) $cm^{-1}$; $\lambda_{max}$ 296 (9832), 284 (9200), 276 (11981), 254 (48450), 248 (37620) nm; δH ($CDCl_3$, 200 MHz) 8.72 (1H, d, $^3J=8$ Hz, aromatic), 8.66 (1H d, $^3J=8$ Hz, aromatic), 8.16 (1H, d, $^3J=8$ Hz, aromatic), 7.75–7.25 (11H, m, aromatic), 4.32 (1H, s, OH), 3.85 (3H, s, $CH_3$); δC ($CDCl_3$, 50 MHz) 175.7 (CO, ester), 141.1, 135.6, 131.3, 130.6, 130.3, 129.8 (quaternary aromatic C's), 129.1, 128.2, 128.1, 127.3, 127.0, 126.9, 126.6, 126.2, 126.1, 122.9, 122.2 (aromatic CH's), 82.1 ($C_1$, quaternary), 53.4 ($CH_3$); m/z (EI) 342, 283, 105.

13-Carboxymethyldibenzo(a,c)fluorene (26)

Treatment of (25) under acidic conditions (conc. $H_2SO_4$, $CH_3COOH$ at 10° C.) led to the formation of (26) in poor yield.

Surprisingly, treatment of (25) with PPA at 110° C., led to the formation of the desired ester (26) in 42% yield.

Polyphosphoric acid (60 g) was heated to 110° C. stirred with a mechanical stirring paddle. To this was added methyl (phenanthren-9-yl,phenyl)hydroxyacetate (5 g, 14.6 mmol). The mixture was stirred for 1 hour at 110° C. The reaction was then cooled to room temperature, diluted with water (150 ml) and extracted with ethyl acetate (4×250 ml). The organic layers were combined, washed with $NaHCO_3$ (10% v/v; 200 ml), water (100 ml) and dried over $MgSO_4$. The solvent was removed in vacuo to give a yellow solid. This crude solid was purified by flash chromatography using toluene as the eluent. After chromatography compound (26) (2.8 g, 60%) could be isolated. This solid was recrystallized from $CH_2Cl_2$/petrol (b.p. 40–60° C.) to afford a white solid, (1.96 g, 42%); m.p. 190–191° C.; (Found: C, 85.2; H, 4.93; $C_{23}H_{16}O_2$ requires: C, 85.2; H, 4.94%); t.l.c. $R_f$(C) 0.50; $R_f$(D) 0.56; $v_{max}$ ($CH_2Cl_2$), 3040, 3020 (CH stretching, aryl), 2970 (CH stretching, alkyl), 1730 (CO, ester), 1610, 1600, 1580 (aromatic rings) $cm^{-1}$; $\lambda_{max}$ 364 (540), 346 (16200), 322 (18360), 268 (64800) nm; δH ($CDCl_3$, 200 MHz), 8.84–8.67 (3H, m, aromatic), 8.36 (1H, d, $^3J=7.8$ Hz, aromatic), 7.98–7.90 (1H, m, aromatic), 7.80–7.35 (7H, m, aromatic), 5.16 (1H, s, CH), 3.63 (3H, s, $CH_3$); δC ($CDCl_3$, 50 MHz), 172.0 (CO, ester), 142.7, 141.9, 137.4, 135.6, 131.1, 130.0, 128.7, 128.4 (quaternary aromatic C's), 128.1, 127.0, 126.7, 126.3, 126.2, 124.3, 124.1, 123.8, 123.3, 123.2, 122.9 (aromatic CH's), 53.4 ($CH_3$), 52.4 (CH); m/z (EI) 324, 265, 262, 132.

13-Hydroxymethyldibenzo(a,c)fluorene (21)

The reduction of ester (26) was achieved in 48% yield using three equivalents of diiobutylaluminum hydride (DIBAL-H) in dichloromethane at –50° C.

Diisobutylaluminum hydride (4.6 ml, 4.62 mmol; 1 M in $CH_2Cl_2$) was added at –65° C. to a solution of 13-carboxymethyl-dibenzo(a,c)fluorene (0.5 g, 1.54 mmol) in dichloromethane (10 ml). The reaction mixture was stirred for 3 h and the temperature maintained between –50° C. and –40° C. A white precipitate was obtained. The reaction mixture was treated with a mixture of acetic acid and water (1:1; 30 ml) and extracted with dichloromethane (3×60 ml). The organic layer was washed with saturated bicarbonate (50 ml), water (30 ml) and dried over $MgSO_4$. The solvent was removed in vacuo to afford a crude solid. This crude solid was purified by flash chromatography using chloroform as the eluent. Compound (21) was obtained as a white solid which was washed with petrol (0.217 g, 48%); m.p. 167–168° C.; (Found: C, 89.0; H, 5.39; $C_{22}H_{16}O$ requires: C, 89.2; H, 5.41%); t.l.c. $R_f$(D) 0.26; $R_f$(E) 0.64; $v_{max}$ ($CH_2Cl_2$) 3610 (free OH), 3490 (H bonded OH), 3060 (CH stretching), 2940, 2890 (CH stretching, alkyl), 1610, 1600, 1580 (aromatic rings) $cm^{-1}$; $\lambda_{max}$ 366 (888), 338 (12728), 322 (14504), 266 (27232), 246 (31968) nm; δH ($CDCl_3$, 200 MHz), 8.88–8.68 (3H, m, aromatic), 8.38 (1H, d, $^3J=7.9$ Hz, aromatic), 8.14–8.08 (1H, m, aromatic), 7.81–7.33 (7H, m, aromatic), 4.45 (2H, m, $H_a$ $CH_2$ and $H_c$), 3.85 (1H, m, $H_b$, $CH_2$), 1.64 (1H, s, OH), δC ($CDCl_3$, 50 MHz), 146.7, 142.5, 139.4, 134.9, 130.9, 130.1, 128.7 (quaternary aromatic C's), 127.5, 126.8, 126.1, 125.9, 125.8, 124.7, 124.2, 124.1, 123.8, 123.4, 122.9 (aromatic CH's), 65.7 (CH), 50.0 (CH); m/z (EI) 296, 265.

This route provides a synthesis of 13-hydroxymethyl-dibenzo(a,c)fluorene (21) in four steps with an overall yield of 10%.

The acetate of both the alcohol (21) and 9-fluorenemethanol (preparations shown below) were then prepared in order to compare their behavior on an HPLC column packed with PGC.

9-Fluorenylmethyl acetate (29) gave a retention time of 3.3 min. (eluted with $CHCl_3$), whereas 13-acetoxymethyl dibenzo(a,c)fluorene (30) under the same conditions, was not completely retained on the column but was slowly eluted.

(29)

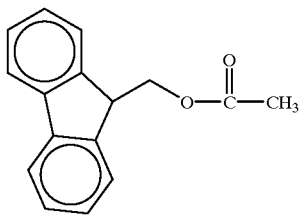

(30)

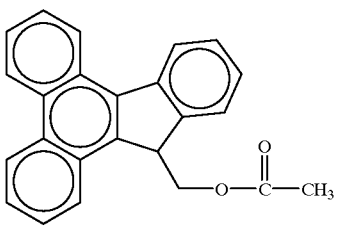

Preparation of 13-Acetoxymethyldibenzo(a,c) fluorene (30)

13-Hydroxymethyldibenzo(a,c)fluorene (215.2 mg, 0.727 mmol) was dissolved in acetic anhydride (5 ml). To this solution was added one drop of sulfuric acid (2M). The reaction mixture was stirred for 30 min. A white precipitate was obtained which was filtered and washed with water (150 ml). The solid was finally dried to constant weight over $P_2O_5$ in a vacuum desiccator to afford 13-acetoxymethyldibenzo (a,c)fluorene as a white solid, (206.3 mg, 84%); m.p. 135–136° C.; (Found: C, 84.9; H, 5,33; $C_{24}H_{18}O_2$ requires: C, 85.2; H, 5.33%; t.l.c. $R_f$(D) 0.57; $R_f$(E) 0.68; $v_{max}$ ($CH_2C_2$) 3030 (CH stretching, aryl) 2980, 2920 (CH stretching, alkyl) 1735 (CO, ester), 1610, 1600, 1570 (aromatic rings) cm$^{-1}$; $\lambda_{max}$ 366 (1184), 338 (25160), 322 (27528), 265 (52688), 246 (53020) nm; δH (CDCl$_3$, 200 MHz), 8.86–8.69 (3H, m aromatic), 9.38 (1H, d, $^3J$=7.9 Hz, aromatic), 8.30–8.25 (1H, m, aromatic), 7.78–7.35 (7H, m, aromatic), 5.16 (1H, dxd, $^3J_{a,c}$=4.1 Hz, $^2J_{a,b}$=10.8 Hz, H$_a$, CH$_2$), 4.56 (1H, dxd, $^3J_{c,a}$=4.1 Hz, $^3J_{c,b}$=9.3 Hz, Hc), 3.76 (1H, dxd, $^2J_{b,a}$=10.8 Hz, $^3J_{b,c}$=9.3 Hz, Hb, CH$_2$), 2.17 (3H, s, CH$_3$); δ$_C$ (CDCl$_3$, 50 MHz) 171.0 (CO, ester), 146.7, 142.1, 138.7, 134.8 131.1, 130.1, 128.7, 128.6 (quaternary aromatic C's), 127.6, 127.0, 126.8, 126.2, 126.1, 125.7, 124.9, 124.8, 124.3, 123.4, 123.3, 122.9 (aromatic CH's), 67.3 (CH$_2$), 46.5 (CH), 20.9 (CH$_3$); m/z (EI) 338, 277, 265, 139, 43.
HPLC: column (ODS3-PL5-393, solvents: A(H$_2$O), B(CH$_3$CN),
conditions: B(50%) 2 min.

B(50%) $\xrightarrow{30 \text{ min.}}$ B (95%)

λ=254 nm, flow rate: 1 ml/min., injection: 5 μl, C=1.42 mg/ml, AUFS=2, retention time: 21.6 min.

Preparation of 9-Fluorenylmethylacetate (29)

9-Fluorenylmethanol (0.215 g, 1.1 mmol) was dissolved in acetic anhydride (5 ml). To this solution was added 2 drops of sulfuric acid (2M). This was stirred for 30 min. The clear solution was poured onto cold water (20 ml). The precipitate obtained was collected on a Buchner filter and dried to constant weight over $P_2O_5$ in a vacuum desiccator to afford 9-fluorenyl-methylacetate as a white solid, (0.175 g, 67%); m.p. 83–84° C.; (Found: C, 80.5; H, 5.98; $C_{16}H_{14}O_2$ requires: C, 80.7; H, 5.88%); t.l.c. $R_f$(D) 0.50; $R_f$(E) 0.68; $v_{max}$ (CH$_2$Cl$_2$) 3030 (CH stretching), 2960, 2910 (CH stretching, alkyl), 1735 (CO, ester), 1610 (aromatic rings) cm$^{-1}$; $\lambda_{max}$ 300 (2476), 290 (2063), 268 (7634) nm; δ$_H$ (CDCl$_3$, 80 MHz), 7.83–7.29 (8H, m, aromatic), 4.46–4.28 (3H, m, CH, CH$_2$), 2.14 (3H, s, CH$_3$); δ$_C$ (CDCl$_3$, 50 MHz), 170.8 (CO, ester), 143.6, 141.1 (quaternary aro-matic C's), 127.6, 126.9, 124.9, 119.9 (aromatic CH's), 66.2 (CH$_2$), 46.5 (CH), 20.8 (CH$_3$); m/z (EI) 238, 178, 165, 149, 60, 43.

HPLC: column (ODS3-PL5-393), solvents: A(H$_2$O), B(CH$_3$CN)

Conditions: B(50%) 2 min.

B(50%) $\xrightarrow{30 \text{ min.}}$ B (95%)

λ=254 nm, flow rate: 1 ml/min.,
injection: 5 μl, C=1.46 mg/ml, AUFS=2, retention time: 8.4 min.

EXAMPLE 2

Synthesis of 17-Hydroxymethyltetrabenzo(a,c,g,i) fluorene (31)

The tetrabenzofluorenyl alcohol (31) was prepared fol-lows:

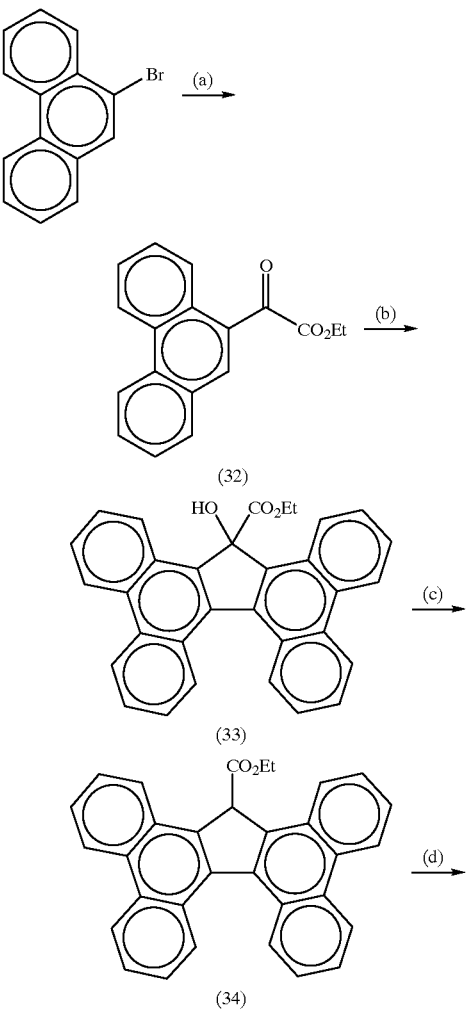

-continued

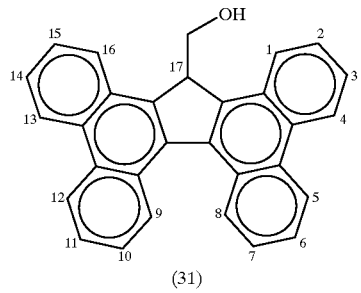

(31)

(a) BuLi, Et$_2$O, r.t., 30 min.; EtOOCCOOEt, Et$_2$O, 0° C.–5° C., 2 h, 63%;
(b) 9-Bromophenanthrene, BuLi, Et$_2$O, r.t., 30 min.; (32), EtO, 0° C.–5° C., 2 h, 46%; (c) PPA, 140° C., 4 h, 49%; (d) DIBAL-H (3 equiv.), CH$_2$Cl$_2$, –65° C., 1 h, 73%.

Ethyl,2-oxo-2-(phenanthren-9'-yl)acetate (32)

The α-keto ester (32) was synthesized by adding 9-phenanthrenyl lithium to a solution of diethyl oxalate (20% excess) in ether at 0° C. The reaction mixture was subsequently heated under reflux for 2 hours. Following purification by flash chromatography, the product was isolated in 23% yield.

The α-keto ester (32) can also advantageously be prepared in ether, by carefully adding 9-phenanthrenyl lithium to a solution of diethyl oxalate (20% excess), between 0° C. and 5° C., and subsequently stirring the reaction at room temperature.

To a stirred solution of 9-bromophenanthrene (5.14 g, 20 mmol) in dry ether (20 ml) was added at 0° C., under nitrogen, a solution of n-butyllithium in hexane (16 ml, 22 mmol; 1.1 equiv; 1.38M titrated) dropwise over 10 min. The reaction was stirred for 1 h at room temperature. The resultant suspension was allowed to settle and the supernatant was removed by syringe. The residue was resuspended in ether (10 ml). This suspension was added, under nitrogen, to a cold (0° C.) solution of diethyl oxalate (3.4 ml, 25 mmol) in ether (100 ml). The temperature was maintained between 0° C. and 5° C. during the addition. The reaction mixture was then stirred for 2 h between 0° C. and 5° C. and finally at room temperature for 2 h. After addition of dilute HCl (100 ml; 10% v/v), the organic layer was separated, combined with ethyl acetate washings (3×100 ml) of the aqueous layer, neutralized with NaHCO$_3$ solution (100 ml; 1M), washed with water (50 ml) and dried over MgSO$_4$. The solvent was removed in vacuo to give an orange oil which was triturated with petrol (b.p. 40° C.–60° C.). Compound (32) was obtained as a yellow solid which was filtered and dried, (3.53 g 63%) m.p. 67–68° C.; (Found: C, 77.5; 5.02; C$_{18}$H$_{14}$O$_3$ requires: C, 77.7; H, 5.04%); t.l.c. R$_f$(A) 0.56, R$_f$(D) 0.52; ν$_{max}$ (CH$_2$Cl$_2$) 3070 (CH stretching, aromatic), 2990, 1910, 2880 (CH stretching, alkyl), 1735 (CO, ester), 1680 (CO, ketone), 1620, 1575 (aromatic rings) cm$^{-1}$; λ$_{max}$ 328 (982), 286 (7784), 252 (34842) nm; δ$_H$ (CDCl$_3$, 200 MHz) 9.04 (1H, m, aromatic), 8.6 (2H, m, aromatic), 8.23, (1H, s, H$_{10}$ aromatic), 7.92 (1H, d, $^3$J=7.6 Hz, aromatic), 7.78–7.59 (4H, m, aromatic), 4.51 (2H, 9, $^3$J=7.1 Hz, CH$_2$), 1.48 (3H, t, $^3$J=7.1 Hz, CH$_3$), δ$_C$ (CDCl$_3$, 50 MHz) 188.5 (CO, ketone), 164.4 (CO, ester), 137.2 (aromatic CH), 132.8 (quaternary aromatic), 130.5, 130.2 aromatic CH's), 129.2, 128.1 (quaternary aromatic C's), 128.0, 127.4, 127.1, 126.3, 122.7, 122.6 (aromatic CH's), 62.3 (CH$_2$), 14.0 (CH$_3$); m/z (EI) 278, 205, 177, 176.

Ethyl(bis-phenanthren-9'-yl)hydroxy acetate (33)

The tertiary alcohol (33) was synthesized in adequate yield under similar conditions using (32) as the keto ester component.

To a stirred solution of 9-bromophenanthrene (2.57 g, 10 mmol) in dry ether (10 ml) was added, at 0° C. under nitrogen, a solution of n-butyllithium in hexane (8 ml, 11 mmol; 1.1 equiv.; 1.38 M titrated) dropwise over 10 min. The reaction mixture was stirred for 1 h at room temperature. This solution was added, under nitrogen, to a cold (0° C.) solution of ethyl,2-oxo-2-(phenanthren-9'-yl)acetate (2.78 g, 10 mmol) in ether (50 ml). The temperature was maintained between 0° C. and 5° C. during the addition. The reaction mixture was finally stirred at room temperature for 2 h. After addition of dilute HCl (50 ml; 10% v/v) the organic layer was separated, combined with ethyl acetate washings (3×250 ml) of the aqueous layer, neutralized with a solution of NaHCO$_3$ (1M; 200 ml), washed with water (200 ml) and finally dried over MgSO$_4$. The solvent was removed in vacuo to give a residue. After purification by flash chromatography using chloroform/petrol (b.p. 40° C.–60° C.) (4:1), the expected product was obtained from the fractions containing material of R$_f$=0.23. After recrystallization from dichloromethane/petrol (b.p. 40° C.–60° C.), a white solid was obtained which was filtered and dried to give compound (33) (2.11 g, 46%); m.p. 188–189° C.; (Found: C, 83.1; H, 5.23; C$_{32}$H$_{24}$O$_3$ requires: C, 84.2; H, 5.26%); t.l.c. R$_f$(E) 0.71; R$_f$(D) 0.48; ν$_{max}$ (CH$_2$Cl$_2$) 3680 (free OH), 3510 (H bonded OH), 3060 (CH stretching, aromatic), 2990, 2940 (CH stretching, alkyl), 1735 (CO, ester), 1600 (aromatic ring) cm$^{-1}$; λ$_{max}$ 332 (629), 300 (25080), 288 (23560), 256 (123120) nm; δ$_H$ (CDCl$_3$, 200 MHz), 8.80–8.69 (4H, m, aromatic), 8.51 (1H, s, H$_{10}$, aromatic), 8.47 (1H, s, H$_{10}$, aromatic), 7.72–7.41 (12H, m, aromatic), 4.46 (1H, s, OH), 4.41 (2H, 9, $^3$J=7.1 Hz, CH$_2$), 1.17 (3H, t, $^3$J=7.1 Hz, CH$_3$), δ$_C$ (CDCl$_3$, 50 MHz) 175.7 (CO, ester), 135.0, 131.4, 130.6, 130.5, 130.1 (quaternary aromatic C's), 129.2, 128.2, 127.3, 126.6, 126.2, 126.1, 122.9, 122.3 (aromatic CH's), 84.3 (C$_1$, quaternary), 62.9 (CH$_2$), 13.8 (CH$_3$); m/z (EI) 383, 206, 177, 176.

17-Carboxyethyltetrabenzo(a,c,g,i)fluorene (34)

Treatment of (33) with polyphosphoric acid at 140° C. led to the formation of the cyclic ester (34) in 49% yield via 4π-electrocyclization of the α-ethoxycarbonyl diaryl cation

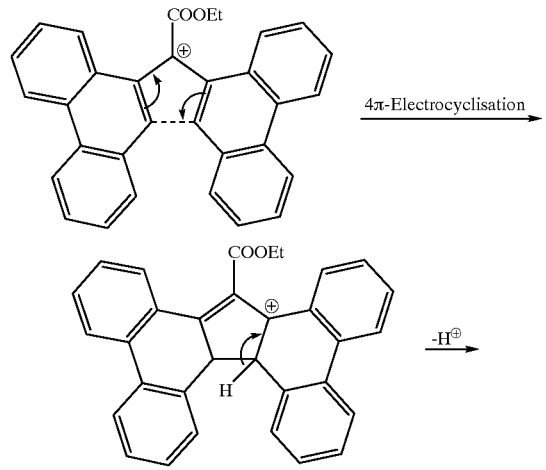

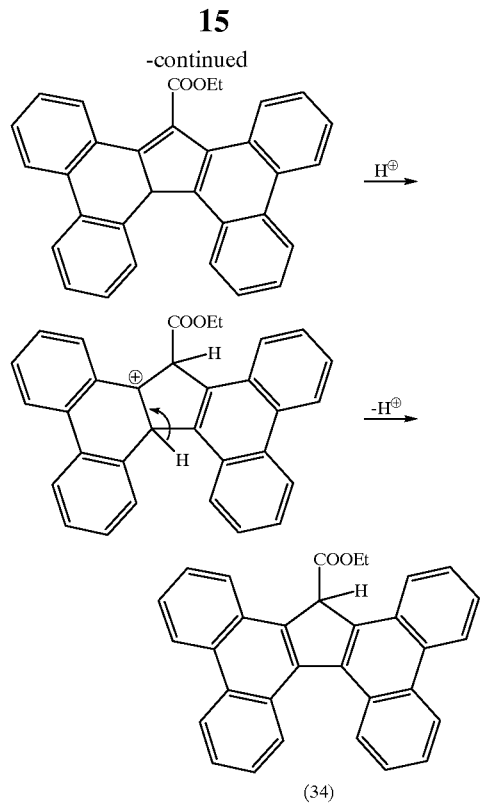

(34)

Purification of (34) is difficult due to the formation of side products. Recrystallization of the crude material following flash chromatography can be carried out.

Polyphosphoric acid (20 g) was placed in a three necked 100 ml round bottom flask equipped with a mechanical stirring paddle. Ethyl (bis-phenanthren-9'-yl) hydroxy acetate (0.402 mg, 0.881 mmol) was then added and the reaction was stirred at 140° C. for 4 h and subsequently at room temperature overnight. The reaction mixture was diluted with water (50 ml) and extracted with ethyl acetate (4×50 ml). The organic layer was neutralized with NaHCO$_3$ (1M; 2×30 ml), washed with water (30 ml) and dried over MgSO$_4$. After removal of the solvent in vacuo a residue was obtained which was purified by flash chromatography (eluent: benzene). The fractions containing material of $R_f$=0.68 were evaporated to give compound (34) as a yellow solid which was washed with petrol, filtered and dried, (189 mg, 49%); m.p. 165–166° C.; (Found: C, 84.4; H, 4.66; $C_{32}H_{22}O_2$ requires: C, 87.7; H, 5.02%); t.l.c. $R_f$(D) 0.68, $R_f$ (F) 0.62; $\nu_{max}$ (CH$_2$Cl$_2$) 3060 (CH stretching, aromatic), 2990, 2960, 2920, 2860 (CH stretching, alkyl), 1810 (CO, lactone), 1735 (CO, ester), 1610, 1500 (aromatic rings) cm$^{-1}$; $\lambda_{max}$ 386 (6371), 370 (7964), 302 (22697), 290 (10894), 254 (42208) nm; $\delta_H$ (CDCl$_3$, 200 MHz) 8.78–8.61 (6H, m, aromatic), 8.28–8.21 (2H, m, aromatic), 7.75–7.55 (8H, m, aromatic), 5.39 (1H, s, CH), 4.04 (2H, q, $^3J$=7.1 Hz, CH), 0.97 (3H, t, $^3J$=7.1 Hz, CH$_3$); $\delta_C$ (CDCl$_3$, 67 MHz) 171.9 (CO, ester), 138.3, 138.2, 131.6, 130.5, 128.6, 127.7 (quaternary aromatic C's), 127.6, 127.1, 126.2, 126.1, 125.0, 123.9, 123.4, 123.2 (aromatic CH's), 61.4 (CH$_2$), 54.9 (CH), 13.8 (CH$_3$); m/z (EI), 438 (M$^+$).

17-Hydroxymethyltetrabenzo(a,c,g,i)fluorene (31)

Reduction of ester (34) to the corresponding alcohol (31) proceeded in a straightforward manner (73% yield). The reaction was carried out in DCM at −65° C. using 3 equivalents of DIBAL-H.

Following flash chromatography and recrystallization from DCM, crystals of (31) were obtained and proved suitable for X-ray analysis.

Diisobutylaluminum hydride (12.3 ml, 12.3 mmol; 3 equiv.; 1M solution in CH$_2$Cl$_2$) was added dropwise at −65° C. to a solution of 17-carboxyethyltetrabenzo(a,c,g,i) fluorene (1.795 g, 4.098 mmol) in dry distilled dichloromethane (25 ml). The temperature was maintained between −65° C. and −60° C. during the addition. The reaction mixture was stirred for 1 h at −65° C. and at room temperature for a further hour. The reaction mixture was cooled to −30° C. An aqueous solution of acetic acid (50 ml; 10% v/v) was then added dropwise. After separation of the two layers, the aqueous phase was extracted with dichloromethane (3×100 ml). The combined organic phases were washed with water (70 ml) and neutralized with NaHCO$_3$. Finally the organic phase was dried over MgSO$_4$ and evaporated to give a crude oil (1.7 g). After purification by flash chromatography using benzene as the eluent, the fractions containing material of $R_f$=0.14 were evaporated to give a yellow solid. This was recrystallized from CH$_2$Cl$_3$/petrol (b.p. 40° C.–60° C.) to afford compound (31) as a yellow solid (1.18 g, 73%); m.p. 202–203° C.; (Found: C, 91.2; H, 4.96; $C_{30}OH_{20}O$ requires: C, 90.9; H, 5.05%); t.l.c. $R_f$ (F) 0.15, $R_f$ (A) 0.18, $R_f$ (B) 0.75; $\nu_{max}$ (CH2Cl$_2$) 3600 (free OH), 3060 (CH stretching, aromatic), 2940, 2900 (CH stretching, alkyl), 1610, 1500 (aromatic rings), 1045 (CO stretching) cm$^{-1}$; $\lambda_{max}$ 380 (10692), 368 (11484), 302 (27324), 290 (21780), 54 (43560) nm; $\delta_H$ (CDCl$_3$, 200 MHz), 8.80–8.63 (6H, m, aromatic), 8.27–8.22 (2H, m, aromatic), 7.73–7.56 (8H, m, aromatic), 5.05 (1H, t, $_3J$=4.3 Hz, CH), 4.49 (2H, d, $^3J$=4.3 Hz, CH), 1.31 (1H, s, OH); $\delta_C$ (CDCl$_3$, 50 MHz), 41.6, 137.3, 131.4, 130.4, 128.5, 127.9 (quaternary aromatic C's), 127.4, 126.9, 126.1, 125.9, 125.0, 124.5, 123.4 (aromatic CH's), 66.5 (CH$_2$), 50.8 (CH); m/z (EI) 396 (M$^+$), 366.

Figure 2:
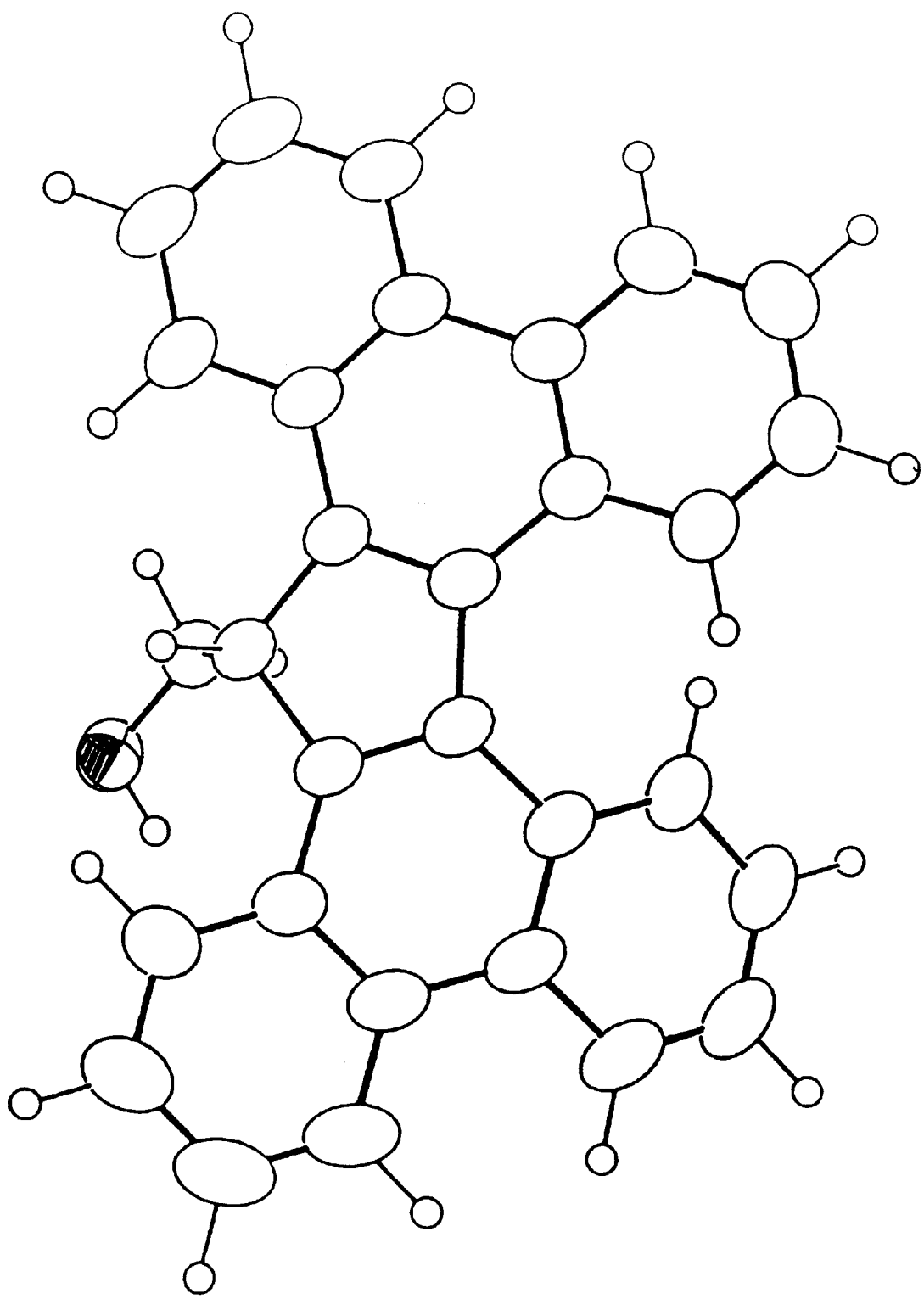

The crystal structure of the alcohol (31) indicates that there are two molecules held together by hydrogen bonding between the two hydroxyl groups. FIGS. 1 and 2 show the crystal structure of the alcohol (31). The exocyclic hydroxymethyl group has two different conformations, probably as this is required for the formation of the hydrogen-bonded dimer. The interaction between H$_8$ and H$_9$ (d=2.0 Å, Van der Waal's radius for hydrogen=1.2 Å) is responsible for a degree of non-planarity in the molecule. However, the molecule is sufficiently planar for the purposes of the invention.

This molecule is chiral if it adopts a fixed orientation, as in the crystal structure. Therefore it is possible that in solution at low temperature, the molecule may also adopt a fixed orientation and be chiral. $^1$H n.m.r. at room temperature in CDCl$_3$ showed a triplet ($\delta$=5.05 ppm) as well as a doublet ($\delta$=4.5 ppm), corresponding to H(17) and the two protons of the methylene group respectively. A probable explanation is that the phenanthrene rings can oscillate rapidly during the acquisition period and consequently the protons of the CH$_2$ group are magnetically equivalent (as are the matched pairs of aromatic protons, e.g., H(2) and H(15)).

Nuclear Overhauser experiments carried out on this compound showed the close through-space interactions between the methylene group and the two aromatic protons H(1) and H(16).

EXAMPLE 3

Synthesis of 17-acetoxymethyltetrabenzo(a,c,g,i) fluorene (35)

17-acetoxymethyltetrabenzo(a,c,g,i)fluorene (35) was easily prepared in 80% yield from alcohol (31) using a large excess of acetic anhydride and a catalytic amount of sulfuric acid.

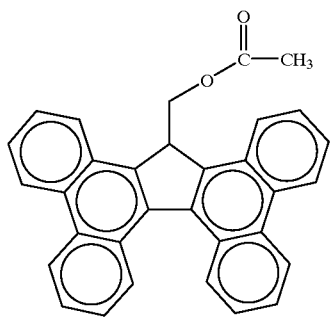

(35)

As expected, the acetate (35) was totally retained when passed through an HPLC column packed with PGC (eluent $CHCl_3$)

17-Hydroxymethyltetrabenzo(a,c,g,i)fluorene (0.207 g, 0.522 mmol) was dissolved in acetic anhydride (4 ml). To this solution was added 2 drops of $H_2SO_4$ (2M). The reaction mixture was stirred for 1 h. Compound (35) was obtained as a yellow solid which was washed with water (80 ml) and dried to constant weight over $P_2O_5$ in a vacuum desiccator (183.8 mg, 80%); m.p. 209–210°, (Found: C, 87.0; H, 5.08; $C_{32}H_{22}O_2$ requires: C, 87.7; H, 5.02%); t.l.c. $R_f$(A) 0.32, $R_f$ (F) 0.22; $\nu_{max}$ ($CH_2Cl_2$) 3060 (CH stretching, aromatic), 1740 (CO, ester), 1610, 1500 (aromatic rings), 1230, 1045 (CO, stretching) cm$^{-1}$; $\lambda_{max}$ 380 (17885), 368 (19345), 302 (45260), 290 (36865), 254 (72271) nm; $\delta_H$ (CDCl$_3$, 80 MHz), 8.83–8.57 (6H, m, aromatic), 8.29–8.17 (2H, m, aromatic), 7.78–7.54 (8H, m, aromatic), 5.12 (1H, t, $^3J=5.5$ Hz, CH), 4.60 (2H, d, $^3J=5.5$ Hz, CH$_2$), 1.84 (3H, s, CH$_3$); $\delta_C$ (CDCl$_3$, 50 MHz) 170.7 (CO, ester), 141.8, 137.0, 131.5, 130.4, 128.6, 128.0 (quaternary aromatic C's), 127.4, 126.8, 126.1, 126.0, 125.0, 124.9, 123.5, 123.3 (aromatic CH's), 67.9 (CH$_2$), 47.1 (CH), 20.7 (CH$_3$); m/z (EI) 438 (M$^+$), 378, 364.

EXAMPLE 4

Conversion of 17-hydroxymethyltetrabenzo(a,c,g,i)fluorene to the chloroformate (37)

The chloroformate (37) is synthesized by the following sequence of reactions: treatment of alcohol (31) with N,N'-bis-trimethylsilyl urea (2.5 equiv) to give the corresponding trimethylsilyl ether (39), followed by reaction of the latter with phosgene. Following recrystallization, the pure product can be obtained in 21% yield.

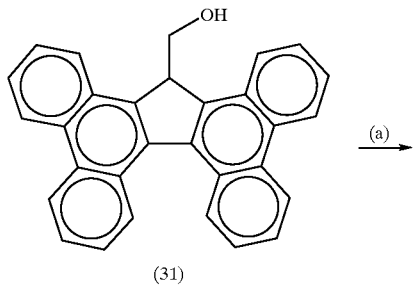

(31)

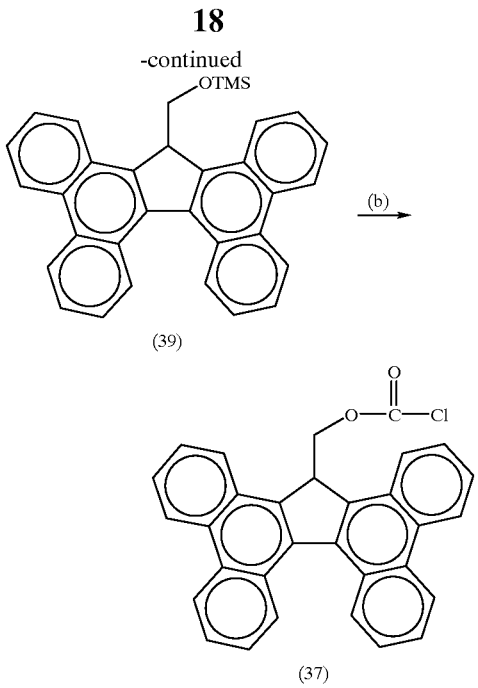

(a) N,N'-bis-trimethylsilyl urea (2.5 equiv), $CH_2Cl_2$, reflux, 3 h, 81%; (b) phosgene (7.5 equiv), $CH_2Cl_2$, reflux, 2 h, 21%.

17-(Trimethylsilyloxymethyltetrabenzo(a,c,g,i) fluorene (39)

A solution of 17-hydroxymethyltetrabenzo(a,c,g,i) fluorene (0.05 g, 0.126 mmol) and N,N'-bis-trimethylsilyl urea (32.3 mg, 0.158 mmol; 2.6 equiv.) in dichloromethane (2 ml) was heated under reflux for 3 h. The precipitated urea was filtered off and washed with dichloromethane (2×1 ml). The solvent was removed in vacuo to give a residue. Purification by wet flash chromatography (benzene/petrol (b.p. 40–60° C.) (75:25)) gave compound (39) (47.8 mg, 81%); m.p. 130–131° C.; (Found: C, 84.2; H, 6.06; $C_{33}H_{28}OSi$ requires: C, 84.6; H, 5.98%); t.l.c. $R_f$ (F) 0.58, $R_f$ (A) 0.51, $R_f$ (G) 0.76; $\delta_H$ (CDCl$_3$, 80 MHz) 8.86–8.62 (6H, m, aromatic), 8.49–8.37 (2H, m, aromatic), 7.79–7.51 (8H, m, aromatic), 5.11 (1H, t, $^3J=5.3$ Hz, CH), 4.13 (2H, d, $^3J=5.3$ Hz, CH$_2$), 0.4 (9H, s, 3×CH$_3$); $\delta_c$ (CDCl$_3$, 67 MHz) 143.4, 136.5, 131.4, 130.3, 129.0, 128.1 (quaternary aromatic C's), 127.4, 126.5, 125.9, 125.8, 125.6, 124.9, 123.5, 123.0 (aromatic CH's), 67.2 (CH$_2$), 51.4 (CH), −1.0 (3×CH$_3$); m/z (EI) 468 (M$^+$), 378, 364.

17-Tetrabenzo(a,c,g,i)fluorenylmethyl chloroformate (37)

To a solution of 17-(trimethylsilyl)oxymethyl-tetrabenzo (a,c,g,i)fluorene (0.177 g, 0.38 mmol) in dichloromethane (5 ml) was added phosgene (1.5 ml, 2.9 mmol; 7.5 equiv; 1.93M in toluene). The reaction mixture was heated under reflux for 2 h and then stirred at room temperature for 48 h, under nitrogen. The solvent was removed in vacuo to give compound (37) as a yellow solid which was recrystallized from dichloromethane/n-hexane (36.9 mg, 21%); m.p. 188–189° C.; (Found: C, 80.9; H, 4.29; N, 0.45; $C_{31}H_{19}O_2Cl$ requires: C, 81.1; H, 4.14%); $\nu_{max}$ (CH$_2$Cl$_2$) 3060 (CH stretching, aromatic), 1775 (CO, chloroformate), 1610, 1500 (aromatic rings), 1160, 1140 (CO stretching) cm$^{-1}$; $\delta_H$ (CDCl$_3$, 200 MHz) 8.79–8.60 (6H, m, aromatic), 8.20–8.15 (2H, m, aromatic), 7.76–7.57 (8H, m, aromatic), 5.17 (1H, t, $^3J$=5.7 Hz, CH), 4.77 (2H, d, $^3J$=5.7 Hz, CH$_2$); $\delta_c$ (CDCl$_3$, 50 MHz) 150.5 (CO, chloroformate), 140.3, 137.2, 131.6, 130.5, 128.2, 127.7 (quaternary aromatic C's), 127.5, 127.0, 126.3, 126.2, 125.1, 124.5, 123.5, 123.4 (aromatic CH's), 74.6 (CH$_2$), 46.5 (CH).

EXAMPLE 5

Preparation of Nα-17-tetrabenzo(a,c,g,i)fluorenylmethoxycarbonylglycine (Tbfmoc Gly OH)

Tbfmoc Gly OH was synthesized in three steps from alcohol (31) via the p-nitrophenyl carbonate (41).

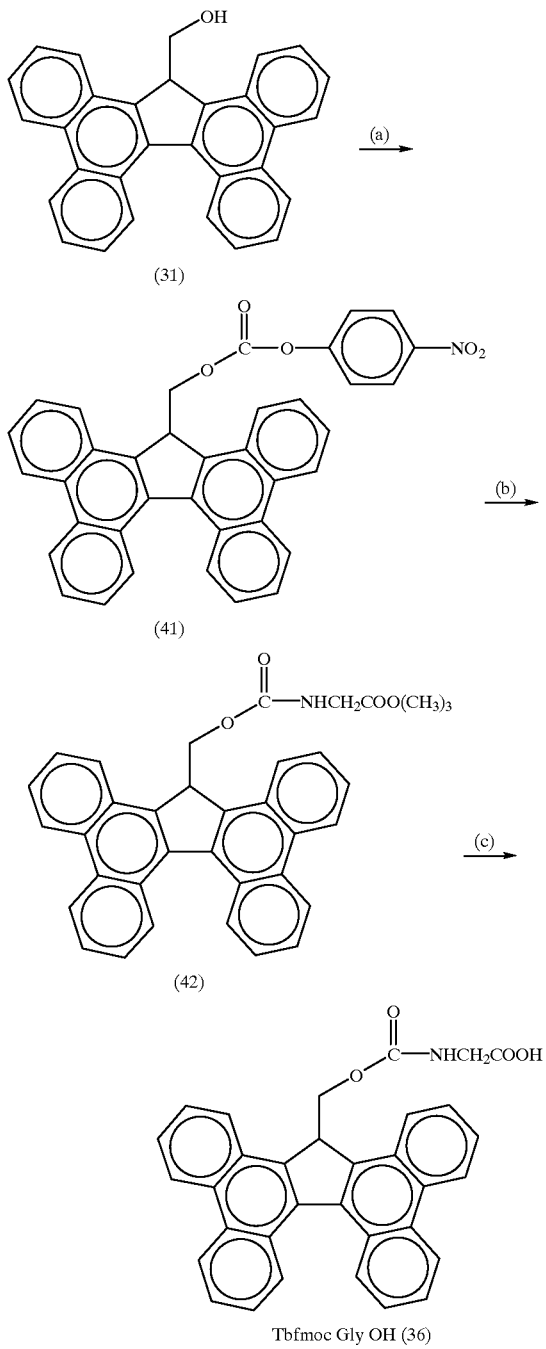

Tbfmoc Gly OH (36)

(a) para-Nitrophenyl chloroformate (2 equiv), N,N'-dimethylaniline (1 equiv), CH$_2$Cl$_2$, r.t., 72 h, 80%; (b) CH$_3$COOH.NH$_2$CH$_2$COOC(Me)$_3$, N,N'-dimethylaniline (2 equiv), CH$_2$Cl$_2$, r.t., 24 h, 79%; (c) para-toluenesulfonic acid (0.3 equiv), CH$_2$Cl$_2$, reflux, 5 h, 90%.

Reaction of commercially available para-nitrophenyl chloroformate (2 equiv) with alcohol (31) and N,N'-dimethylaniline gave the mixed carbonate (41) in 80% yield. This material was in turn reacted with the acetate salt of glycine tert-butyl ester in the presence of two equivalents of N,N'-dimethylaniline to afford the protected glycine tert-butyl ester (42) (79%). Simple hydrolysis of the latter using p-toluenesulphonic acid in refluxing DCM gave the desired acid (36) in 90% yield. This is an easy synthesis of Tbfmoc Gly OH using mildly basic conditions in a 57% overall yield based on alcohol (31).

17-Tetrabenzo(a,c,g,i)fluorenylmethyl-p-nitrophenyl carbonate (41)

To a solution of 17-hydroxymethyltetrabenzo-(a,c,g,i) fluorene (0.05 g, 0.126 mmol) and p-nitrophenyl chloroformate (35.5 mg, 0.175 mmol; 1.4 equiv.) in dichloromethane (2 ml) was added N,N'-dimethylaniline (16 μl, 0.126 mmol). The reaction was stirred at room temperature, under nitrogen, for 24 h. The reaction was driven to completion by adding more p-nitrophenyl chloroformate (45 mg, 0.223 mmol; 1.7 equiv.) and by stirring at room temperature for a further 48 h. After purification by flash chromatography using toluene as the eluent, the fractions containing material of $R_f$=0.29 were evaporated to give a yellow oil. Trituration in petrol (b.p. 40–60° C.) gave compound (41) as a yellow solid (56.5 mg, 80%); m.p. 139–140° C.; (Found: C, 77.7; H, 3.94; N, 2.29; C$_{37}$H$_{23}$NO$_5$ requires: C, 79.1; H, 4.10; N, 2.49%); t.l.c. $R_f$ (C) 0.29, $R_f$ (A) 0.16; $\nu_{max}$ (CH$_2$Cl$_2$) 3060 (CH stretching, aromatic), 2960, 2930, 2880 (CH stretching, alkyl), 1770 (CO, carbonate), 1620, 1600, 1495 (aromatic rings), 1530, 1350 (conjugated nitro-NO$_2$), 1215 (CO stretching), 860 (CH bending, p-disubstituted) cm$^{31}$ $^1$; $\lambda_{max}$ 366 (20035) 301 (52092), 289 (48085), 260 (85751), 252 (88957) nm; δH (CDCl$_3$, 200 MHz) 8.79–8.76 (4H, m, aromatic), 8.61–8.57 (2H, m, aromatic), 8.33–8.16 (2H, m, aromatic), 7.91 (2H, d, $J_{AB}$=8.9 Hz, p-nitrophenyl), 7.76–7.56 (8H, m, aromatic), 6.64 (2H, d, $J_{AB}$=8.9 Hz, p-nitrophenyl), 5.14 (1H, t, $^3J$=4.7 Hz, CH), 4.96 (2H, d, $^3J$=4.7 Hz, CH); δc (CDCl$_3$, 50 MHz) 154.9 (CO, carbonate), 151.6 (quaternary aromatic C$_{1'}$), 144.9 (quaternary aromatic C$_{4'}$), 140.3, 137.4, 131.5, 130.4, 128.3, 127.7 (quaternary aromatic c's), 127.4, 127.0, 126.2, 125.1, 124.7, 124.1, 123.5, 121.2 (aromatic CH's), 125.3 (aromatic CH$_{2',6'}$), 121.4 (aromatic CH$_{3',5'}$), 71.2 (CH$_2$), 46.8 (CH); m/z (EI) 378, 139, 44; (FAB) 561 (M$^+$), 379. HRMS 561.15759, C$_{37}$H$_{23}$NO$_5$ requires: 561.15761 ( ) <1 ppm.

Nα-17-Tetrabenzo(a,c,g,i)fluorenylmethoxycarbonyl glycine tert-butyl ester (42)

To a solution of 17-tetrabenzo(a,c,g,i)fluorenylmethyl-p-nitrophenyl carbonate (39.2 mg, 0.07 mmol) and glycine tert-butyl ester acetate salt (14.7 mg, 0.077 mmol; 1.1 equiv.) in dichloromethane (1.5 ml) was added N,N'-dimethyl aniline (18 μl, 0.14 mmol; 2 equiv). The reaction mixture was stirred at room temperature, under nitrogen, for 72 h. After addition of water (10 ml) and acidification with KHSO$_4$ (2M; pH=1), the reaction mixture was extracted with dichloromethane (3×15 ml), washed with water (3×20 ml) and dried over MgSO$_4$. The solvent was removed in vacuo to give an orange oil which was triturated in ether. A yellow solid was obtained which was filtered, washed with petrol (b.p. 40–60° C.) and dried to give compound (42)

(30.6 mg, 79%); m.p. 170–171° C.; (Found: C, 79.7; H, 5.51; N, 2.33; $C_{37}H_{31}NO_4$ requires: C, 80.3; H, 5.60; N, 2.53%); t.l.c. $R_f$ (H) 0.79, $R_f$ (I) 0.95; $v_{max}$ ($CH_2Cl_2$) 3440 (secondary amide NH), 3060 (CH stretching, aromatic), 2940 (CH stretching, alkyl), 175 (CO, urethane, ester and slide I), 1600, 1500 (aromatic rings), 1520 (amide II), 1340 (OH bonding) $cm^{-1}$, 1220, 1160, 1110 (CO stretching), 865, 850 (out of plane CH bonding); $\lambda_{max}$ 384 (16323), 367 (17656), 302 (42641), 290 (34313), 262 (62296) nm; δH ($CDCl_3$, 80 MHz) 8.85–8.60 (6H, m, aromatic), 8.39–8.28 (2H, m, aromatic), 7.81–7.56 (8H, m, aromatic), 5.27 (1H, t, $^3J$=6 Hz, CH), 4.98 (1H, s broad, NH), 4.61 (2H, d, $^3J$=6 Hz, $CH_2$), 3.74 (2H, d, $^3J$=6 Hz, $CH_2$ glycine), 1.44 (9H, s, $CH_3$×3); δc ($CDCl_3$, 50 MHz) 168.7 (CO, ester), 156.1 (CO, urethane), 141.9, 136.7, 131.5, 130.3, 128.7, 127.9 (quaternary aromatic C's), 127.4, 126.8, 126.0, 125.8, 125.3, 124.9, 123.5, 123.1 (aromatic CH's), 82.0 (quaternary C, $CMe_3$), 69.0 ($CH_2$), 47.5 (CH), 43.2 ($CH_2$, glycine), 27.9 ($CH_3$×3); m/z (FAB) 553, 379. HRMS 553.22527, $C_{37}H_{31}NO_4$ requires 553.22529 ( ) <1 ppm.

Nα-17-Tetrabenzo(a,c,g,i)fluorenylmethoxycarbonyl glycine (Tbfmoc Gly OH) (36)

A solution of Nα-17-tetrabenzo(a,c,g,i)fluorenylmethoxycarbonyl glycine tert-butyl ester (0.39 g, 0.708 mmol) and p-toluenesulphonic acid (39.2 mg, 0.206 mmol) in dichloromethane (15 ml) was heated under reflux for 4.5 h, during which time a precipitate was formed. This precipitate was filtered, washed with dichloromethane (2×15 ml) and dried to afford compound (36) (319 mg, 90%); m.p. 240–241° C.; (Found: C, 77.7; H, 4.5; N, 2.0; $C_{33}H_{23}NO_4$ requires: C, 79.7; H, 4.63; N, 2.82%); t.l.c. Rf (H) 0.56, $R_f$ (I) 0.80; $v_{max}$ (KBr disc) 3320 (NH stretching), 3060 (CH stretching, aromatic), 1735 (CO, acid), 1710 (CO, urethane), 1680 (amide I), 1540 (amide II), 1610, 1500 (aromatic rings), 1435 (CH deformations, alkyl), 1310 (OH bending), 1260, 1240,1175, 1160, 1040 (CO stretching), 1000, 745, 720 (out of plane CH bending) $cm^{-1}$; $\lambda_{max}$ 382 (21744), 368 (23297), 303 (55913), 291 (45041); 264 (82005), 255 (88839) nm; δH (d-dioxan, 200 MHz), 9.05–8.97 (4H, 2×d, aromatic), 8.83 (2H, d, $^3J$=7.8 Hz, aromatic), 8.64 (2H, d, $^3J$=7.8 Hz, aromatic), 7.95–7.74 (8H, m, aromatic), 6.53 (1H, t, $^3J$=5.8 Hz, NH), 5.61 (1H, t, $^3J$=5.1 Hz, CH), 4.78 (2H, d, $^3J$=5.1 Hz, $CH_2$), 3.96 (H, d, $^3J$=5.8 Hz, $CH_2$ glycine); δc (d-dioxan, 50 MHz) 170.6 (CO, acid), 156.2 (CO, urethane), 142.5, 136.2, 131.3, 130.0, 128.7, 127.7 (quaternary aromatic C's), 127.0, 126.5, 125.6, 125.4, 124.5, 123.3, 122.8 (aromatic CH's), 68.3 ($CH_2$), 47.6 (CH), 41.5 ($CH_2$, glycine); m/z (FAB) 497, 397. HRMS 498.17053, $C_{33}H_{24}NO_4$ requires 498.17052 ( ) <1 ppm. HPLC: column (RP 18), solvents: A ($H_2O$/TFA(0.1%)), B ($CH_3CN$/TFA (0.1%)); conditions: B (75%), A (25%); λ=229 nm, AUFS=2 or λ=368 nm, AUFS=1; flow rate: 1 ml/min; injection: 25 μl, C=1.3 mg/ml (dioxan/water (1:1)), retention time: 5.4 min.

EXAMPLE 6

Solid Phase Synthesis

All protected amino acid derivatives were purchased from Novabiochem and have L-stereochemistry. Solid phase peptide synthesis was carried out on an Applied Biosystems 430A peptide synthesizer. The DMF used was supplied by Rathburn Chemicals Ltd. (peptide synthesis grade). The first residue of each sequence (i.e., the C-terminal residue) was coupled to the p-alkoxybenzyl alcohol resin outside the synthesizer. The extent of coupling was determined by deprotecting a small sample of the loaded resin and quantitatively checking the olefin produced by UV at 300 nm in the case of Fmoc-peptides and at 364 nm in the case of Tbfmoc-peptides. Each residue was coupled twice (2 equiv.), firstly by the symmetrical anhydride method and secondly by the HOBt active ester method ('double coupling') (except Arg, Asn, Gln double coupled via HOBt ester and Gly coupled once via symmetrical anhydride (4 equiv.). Preformed symmetrical anhydrides were prepared from Fmoc-amino acids (1 mmol) and DICI (0.5 mmol) with an activation time of 15 minutes, and HOBt esters from Fmoc-amino acids (0.5 mmol), DICI (0.5 mmol) and HOBt (0.5 mmol) with an activation time of 30 minutes. Coupling reactions were carried out over a period of 30–60 minutes. Capping of unreacted amino functions was performed for 6 minutes using acetic anhydride and pyridine in DMF. Deprotection of the Fmoc-peptide-resin was achieved over a 12 minute period (5+3+3+1 minutes) using a solution of 20% piperidine in DMF. The resin was washed thoroughly with DMF at the end of each cycle. As a rough monitor of the couplings, the product solution from the deprotection steps was fed through an ultraviolet detector (313 nm) and its absorption recorded to give a series of peaks. Removal of peptides from the resin and simultaneous cleavage of side chain protecting groups were performed using a mixture of trifluoroacetic acid/water/scavenger (95:5:5) for 2–3 hours. Chromatography of Nα-protected peptides was carried out using graphitized carbon (PGC 220–224; 150–180 pm, 100 $m^2$/g) in a glass column. HPLC was carried out on Waters system using an ABI aquapore Prep 10 C-18 300 Å pore size 20 μm spherical silica (10 mm ID×250 mm) column for preparative separations and an ABI RP 18 aquapore OD 300 7 μm spherical silica (4.6 mm ID×220 mm) column for analytical separations. A gradient was used, as specified in parentheses, between solvent A (0.1% TFA in water) and solvent B (0.1% TFA in acetonitrile). The flow rate was 1 ml/min for analytical HPLC and 5 ml/min for preparative HPLC. Elution of the samples was monitored by ultraviolet absorption at 14 nm. Amino acid analyses were carried out on a LKB 4150 alpha amino acid analyzer following sealed tube hydrolysis in constant boiling hydrochloric acid at 110° C. for 18–36 hours.

Synthesis of Fmoc Gly Ser Met Val Leu Ser OH SEQ ID NO:1 and Tbfmoc Gly Ser Met Val Leu Ser OH SEQ ID NO:1 and Comparison of Properties Thereof a. Synthesis of Fmoc Gly Ser Met Val Leu Ser OH SEQ ID NO:1

The protected resin-bound peptide Fmoc Ser (O'Bu) Met Val Leu Ser (O'Bu) SEQ ID NO:2 (43) was prepared on a peptide synthesizer using an orthogonal strategy. Fmoc was used for the temporary protection of the amine function of each amino acid and was removed before each coupling with a 20% piperidine in DMF solution. The side-chain function of serine was protected with the t-butyl group. The coupling procedures involved a symmetrical anhydride followed by an HOBt ester coupling. Acetic anhydride and pyridine were used to acetylate any unreacted amino functions. The Merrifield resin was employed with the p-alkoxybenzylalcohol group as the linker.

Fmoc Gly Ser Met Vat Leu Ser OH SEQ ID NO:1 (44) was synthesized from the resin-bound peptide (43) via the series of reactions outlined below.

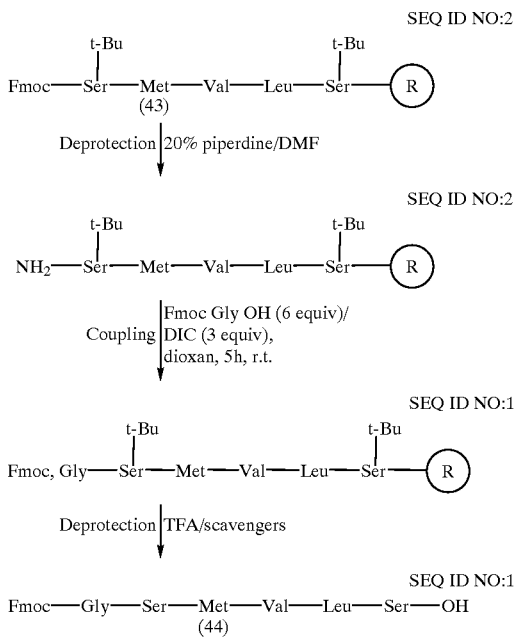

After deprotection of the Fmoc group under basic conditions the amino-terminus of the peptide SEQ ID NO:2 was coupled in dioxan to Fmoc Gly OH via its symmetrical anhydride (3 equiv) with a coupling efficiency of 88%. Cleavage of the hexapeptide SEQ ID NO:1 from the resin and removal of the t-butyl groups was carried out using TFA, and in the presence of ethylmethylsulphide and anisole as cation scavengers. After removal of the solvent in vacuo the peptide SEQ ID NO:1 was finally precipitated with ether, filtered off and dried. Purification using HPLC was carried out using dioxan in which the peptide SEQ ID NO:1 was soluble at approximately 1.5 mg/ml. Preparative HPLC gave the peptide SEQ ID NO:1 (44) together with a trace of the sulfoxide derivative, as indicated by mass spectrometry (MH+16$^+$). The identity of the peptide SEQ ID NO:1 was confirmed by mass spectrometry and amino acid analysis.

Nα-9-Fluorenylmethoxycarbonyl
glycylserylmethionylvalylleucylserine, Fmoc Gly
Ser Met Val Leu Ser OH SEQ ID NO:1 (44)

The resin-bound peptide Fmoc Ser (O$^t$Bu) SEQ ID NO:2 Met Val Leu Ser (O$^t$Bu) (130.5 mg, 0.05 mmol) was sonicated in a solution of 20% piperidine in N,N-dimethylformamide (5 ml) for 20 min., then filtered and finally washed well with N,N-dimethyl-formamide, dichloromethane and dioxan. Fmoc Gly OH (89.2 mg, 0.3 mmol; 6 equiv.) was dissolved in dioxan (2 ml); 1,3-diisopropylcarbodiimide (47 µl, 0.3 mmol; 6 equiv.) was then added and the reaction mixture was sonicated for 5 min. This solution was then added to the resin-bound peptide SEQ ID NO:2 previously swollen in dioxan (1 ml). The reaction mixture was sonicated for 4.5 h. The resin-bound peptide SEQ ID NO:1 was filtered, washed with dichloromethane, ether, and dried (129.8 mg); product resin functionality in mmol/g: 0.334, resin loading/coupling percentage: 88; $A_{300}$ nm=0.76 (resin-peptide SEQ ID NO:1: 2.52 mg). To a mixture of resin-peptide (126.1 mg, 0.042 mmol) anisole (0.25 ml), ethylmethylsulphide (0.5 ml) and water (0.25 ml) was added trifluoroacetic acid (10 ml). The reaction mixture was sonicated for 2 h. The resin was filtered, washed with trifluoroacetic acid (2×1 ml) and chloroform (4 ml). The solvent was removed in vacuo to give a residue. The peptide SEQ ID NO:1 was precipitated on addition of ether, filtered, washed with ether and dried (42.7 mg); (Found: Ser$_2$ 1.90, Gly$_1$ 1.05, Val$_1$ 0.99, Met$_1$ 1.02, Leu$_1$ 1.01); m/z (FAB) 853, 837, 815 (MH$^+$). HRMS 815.36488, $C_{39}H_{55}N_6O_{11}S_1$ requires: 815.36492 ( ) <1 ppm. HPLC: column RP 18, solvents: A (H$_2$O/TFA (0.1%)), B (CH$_3$CN/TFA (0.1%)); conditions:

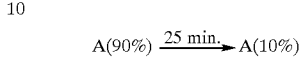

λ=229 nm; AUFS=0.2; flow rate: 1 ml/min; injection: 25 µl (C=0.4 mg/0.5 ml (dioxan)); retention time: 14.2 min.

b. Synthesis of Tbfmoc Gly Ser Met Val Leu Ser OH SEQ ID NO:1

Tbfmoc Gly Ser Met Val Leu Ser OH SEQ ID NO:1 (45) was then prepared from the resin-bound peptide SEQ ID NO:2 (43) via a similar method.

Tbfoc Gly OH was coupled in dioxan with an 80% coupling efficiency. Removal of the peptide SEQ ID NO:1 from the resin and t-butyl cleavage were carried out with TFA in the presence of the same scavengers. The peptide SEQ ID NO:1 was finally precipitated with ether, filtered off and dried (69% yield).

The peptide SEQ ID NO:1 was purified as before. A fresh solution of the crude peptide SEQ ID NO:1 in dioxan gave one peak on HPLC, but on standing (30 min.) the same solution gave two peaks corresponding to the desired peptide SEQ ID NO:1 and the sulfoxide derivative. The facile oxidation of methionine to the sulfoxide might be due to the presence of peroxides in the dioxan. After isolation of these two peptides SEQ ID NO:1 by preparative HPLC, these assignments were confirmed by mass spectrometry (MH$^+$ and MH+16$^+$) and amino acid analysis.

Nα-17-Tetrabenzo(a,c,g,i)fluorenylmethoxy-
carbonylglycylserylmethionylvalylleucylserine
(Tbfmoc Gly Ser Met Val Leu Ser OH) SEQ ID
NO:1 (45)

The resin-bound peptide Fmoc Ser (O$^t$Bu) Met Val Leu Ser (O$^t$BU) SEQ ID NO:2 (65.3 mg, 0.025 mmol) was sonicated in a solution of 20% piperidine in DMF (5 ml) for 20 min. The resin-bound peptide SEQ ID NO:2 was then filtered and washed well with DMF, dichloromethane and dioxan. Tbfmoc Gly OH (74.5 mg, 0.15 mmol; 6 equiv.) was sonicated for 30 min. in dioxan (2 ml). 1,3-Diisopropylcarbodiimide (23.5 µl, 0.15 mmol; 6 equiv.) was then added and the reaction mixture was sonicated for 5 min. This solution was then added to the resin-bound peptide SEQ ID NO:2 previously swollen in dioxan (1 ml). The reaction mixture was sonicated for 5 h. The resin was filtered, washed well with dichloromethane, dioxan and ether, and then dried (58.3 mg); product resin functionality in mmol/g: 0.28; resin loading/coupling percentage: 80; $A_{364}$ nm=0.43 (resin-bound peptide SEQ ID NO:1: 0.85 mg). To a mixture of resin-bound peptide (57.3 mg, 0.016 mmol), anisole (0.5 ml), ethylmethylsulphide (0.25 ml) and water (0.5 ml), was added trifluoroacetic acid (5 ml). The reaction mixture was sonicated for 2 h. The resin was filtered and washed with trifluoroacetic acid (1 ml) and chloroform (4 ml) and the solvent was removed in vacuo. Trituration of the residue in ether gave the desired peptide SEQ ID NO:1 as a yellow solid which was filtered, washed well with ether and dried (17.2 mg, 69%); (Found: $Ser_2$ 1.8, $Gly_1$ 0.08, $Val_1$ 1.00, $Met_1$ 0.96, $Leu_1$ 1.00; m/z (FAB) 1053, 1037, 1015 ($MH^+$). HRMS 1015.42761, $C_{55}H_{63}N_6O_{11}S_1$ requires: 1015.42752 ( ) <1 ppm. HPLC: column RP18, solvents: A ($H_2O$/TFA (0.1%)); B ($CH_3CN$/TFA (0.1%); conditions: A;

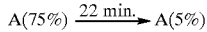

$\lambda$=229 nm; AUFS=1; flow rate: 1 ml/min; injection: 25 $\mu$l (C=0.2 mg/0.2 ml (dioxan)); retention time: 16.1 min.

c. Behavior of Tbfmoc and Fmoc Derivatives on PGC

The retention of both Fmoc Gly OH and Tbfmoc Gly OH was compared on a column packed with graphitized carbon.

A solution of Fmoc Gly OH (10.2 mg, 34.3 $\mu$mole) in dioxan was loaded on a 6 mm diameter column packed with PGC (1.5 g). Only 15 ml of dioxan was required to elute the compound completely (as monitored by t.l.c.). In contrast, when Tbfmoc Gly OH (10.2 mg, 20.5 $\mu$mole) was loaded under the same conditions, none of this material was eluted in the first 35 ml. Indeed the total volume of dioxan needed to elute the compound was 300 ml.

The behavior on a graphitized carbon column of Fmoc Gly Ser Met Val Leu Ser OH SEQ ID NO:1 (44) was then compared with the Tbfmoc derivative SEQ ID NO:1 (45). To increase the overall retention time, a mixture of dioxan/water (2:1) was used to elute both peptides. After loading a solution of the Fmoc hexapeptide SEQ ID NO:1 (9.2 mg, 11.3 $\mu$mole) in a mixture of dioxan/water (2:1) onto the column, the peptide SEQ ID NO:1 was eluted completely with 75 ml of the solvent mixture. In contrast, the Tbfmoc derivative SEQ ID NO:1 (10.5 mg, 10.3 $\mu$mole) was not eluted at all in the first 80 ml of solvent and was subsequently only very slowly eluted from the column.

d. Deprotection of the Tbfmoc Group

Deprotection of the Tbfmoc group from the peptide, while still retained on the graphitized carbon column was carried out.

The deprotection was carried out using 20% piperidine in a mixture of dioxan/water (2:1). Under these conditions the Tbfmoc hexapeptide SEQ ID NO:1 was totally deprotected. The free peptide (H Gly Ser Met Val Leu Ser OH SEQ ID NO:1 (46)) was eluted and was monitored by t.l.c. using ninhydrin to reveal the amino function. The subsequent isolation of the product was simple; the piperidine and solvents were removed in vacuo and the peptide SEQ ID NO:1 was precipitated with ether, filtered and dried (85%). Mass spectrometry showed both the presence of the peptide SEQ ID NO:1 ($MH^+$) and the sulfoxide derivative ($MH+16^+$). Amino acid analysis confirmed the composition of the peptide SEQ ID NO:1.

Glycylserylmethionylvalylleucylserine (H Gly Ser Met Val Leu Ser OH) SEQ ID NO:1 (46)

A solution of Tbfmoc Gly Ser Met Val Leu Ser OH SEQ ID NO:1 (29.2 mg, 8.8 $\mu$mol) in a mixture of dioxan and water (2:1; 15 ml) was loaded on a 9 mm diameter column packed with graphitized carbon (4 g). The column was then eluted with a mixture of dioxan and water (2:1; 60 ml). The deprotection was carried out by eluting the column with 20% piperidine in a mixture of dioxan and water (2:1; 20 ml). The fractions containing the peptide SEQ ID NO:1 (monitored by t.l.c., $R_f$=0 ($MeOH/CHCl_3/CH_3COOH$ (1:9:0.5)) using ninhydrin) were combined and evaporated to give a residue. The peptide SEQ ID NO:1 was precipitated with ether, filtered and dried (14.5 mg, 85%); (Found: $Ser_2$ 1.92, $Gly_1$ 0.98, $Val_1$ 1.03, $Met_1$ 0.87, $Leu_1$ 1.02; m/z (FAB) 609, 593 ($MH^+$). HRMS 593.29689, $C_{24}H_{45}O_9N_6S$ requires: 593.29685 ( ) <1 ppm.

Finally, the tetrabenzofluorene olefin or its piperidine adduct, the by-products from the deprotection step, were removed from the column by eluting with hot dioxan.

EXAMPLE 7

Synthesis of Fmoc Ubiquitin (54–76) OH SEQ ID NO:4 and Tbfmoc Ubiquitin (53–76) OH SEQ ID NO:3 and Comparison of Properties Thereof a. Synthesis of Fmoc Ubiquitin (54–76) OH SEQ ID NO:4

The resin-bound peptide Fmoc ubiquitin (54–76) SEQ ID NO:4 (47) was prepared on a peptide synthesizer under the conditions described in Example 6(a). Most coupling procedures involved a symmetrical anhydride followed by an HOBt ester coupling in a mixture of DMF/dioxan (1:1) as the solvent.

b. Synthesis of Tbfmoc Ubiquitin (53–76) OH SEQ ID NO:3

Tbfmoc ubiquitin (53–76) OH SEQ ID NO:3 (48) was synthesized from the resin-bound peptide SEQ ID NO:4 (47) as depicted below.

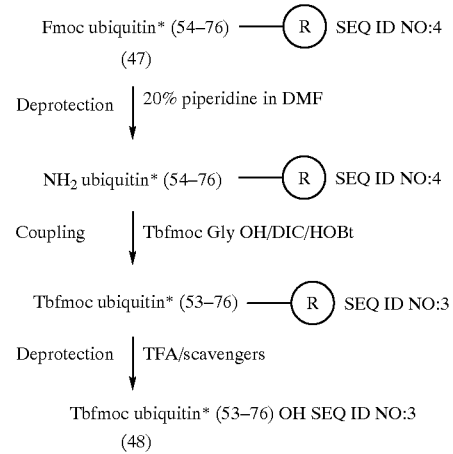

The resin-bound peptide Fmoc ubiquitin (54–76) SEQ ID NO:4 was initially treated with a mixture of acetic anhydride/pyridine (1:1) in order to cap any amino functions. After deprotection in basic conditions the peptide SEQ ID NO:4 was coupled in dioxan to Tbfmoc Gly OBt ester (4 equiv), generated in situ from DIC and HOBt, with a coupling efficiency of 88%. After final cleavage using TFA in the presence of anisole and thioanisole as cation scavengers, the Tbfmoc ubiquitin peptide SEQ ID NO:3 (48) was precipitated with ether (96% yield).

N$\alpha$-(17-Tetrabenzo(a,c,g,i)fluorenylmethoxy-
carbonyl)glycylarginylthreonylleucylseryllaspartyl-
tyrosylasparagyl isoleucylglutaminyllysylglutamyl-
serylthreonylleucylhistidylleucylvalylleucylarginyl
leucylarginylglycylglycine (Tbfmoc-ubiquitin
(53–76) OH) SEQ ID NO:3 (48)

To the Fmoc-ubiquitin (54–76) SEQ ID NO:4 resin bound peptide (150 mg, 2.65 $\mu$mol) in DMF (1 ml) was added acetic anhydride (21.4 μl, 226 μmol; 10 equiv.) and pyridine (18.2 μl, 226 μmol; 10 equiv.). The reaction mixture was sonicated for 30 min. After filtration and washing with DMF and ether, the resin-bound peptide SEQ ID NO:4 was sonicated for 15 min. in a solution of 20% piperidine in DMF (25 ml). The resin bound peptide SEQ ID NO:4 was then filtered and washed well with DMF and ether. Tbfmoc Gly OH (45 mg, 0.09 mmol; 4 equiv.) was sonicated for 30 min. in dioxan (1.5 ml) until complete dissolution. To this solution was added 1,3-diisopropylcarbodiimide (14 μl, 0.09 mmol; 4 equiv.) and 1-hydroxybenzotriazole (12.2 mg, 0.09 mmol; 4 equiv.). The reaction mixture was sonicated for 2 min. This solution was then added to the resin bound peptide SEQ ID NO:4 previously swollen for 30 min. in dioxan (1.5 ml). After sonication for 3.5 h, the resin bound peptide SEQ ID NO:3 was filtered, washed with dioxan and ether and dried overnight in a desiccator under vacuum (148.1 mg).

Substitution Efficiency

The Tbfmoc resin bound peptide SEQ ID NO:3 (2.1 mg) was sonicated for 30 min. in a solution of 20% triethylalmine in DMF (10 ml). The specific absorption at 364 nm was recorded and the following results were derived from it: product resin functionality in mmol/g: 0.133; resin loading/coupling percentage: 88; $A_{364}$ nm=0.505 (resin bound peptide: 2.1 mg). To the resin bound Tbfmoc-peptide SEQ ID NO:3 (146 mg) was added water (75 μl), thioanisole (75 μl), anisole (75 μl) and trifluoroacetic acid (3 ml). The reaction mixture was sonicated for 2.5 h. The resin was filtered, washed with TFA (2×0.5 ml) and chloroform (2×1 ml), and dried (24 mg). The filtrate was evaporated under reduced pressure to give a residue. Trituration in ether gave the crude peptide SEQ ID NO:3 as a yellow solid which was chilled overnight, filtered and dried (68.5 mg). A suspension of crude Tbfmoc-ubiquitin SEQ ID NO:3 (53–76) (12 mg) in $CH_3CN/H_2O$ (1:1; 0.1% TFA; 12 ml) was then sonicated for 2 h until complete dissolution had occurred. Purification of this product was finally achieved by preparative HPLC using a reverse phase C-18 column (10×250 mm) with a gradient of A:B, 20 to 80% B over 25 min. and ultraviolet detection at 214 nm, to yield pure Tbfmoc ubiquitin SEQ ID NO:3 (53–76) after lyophilization as a white powder (4.5 mg); amino acid analysis: $Asx_2$ 2.14, $Thr_2$ 1.94, $Ser_2$ 1.87, $Glx_2$ 2.38, $Gly_3$ 2.73, $Val_1$ 1.14, $Ile_1$ 0.94, $Leu_5$ 5.02, $Tyr_1$ 0.94, $His_1$ 1.01, $Lys_1$ 0.94, $Arg_3$ 2.94; m/z (FAB) 3147.4 ($MH^+$), HRMS 3149.64063, $C_{149}H_{219}N_{38}O_{38}$ requires: 3149.64048 ( ) <1 ppm;

HPLC (A:B, A (90%) $\xrightarrow{25\text{ min.}}$ A (10%);

214 nm; C=0.2 mg/0.2 ml (A), injection: 25 μl) $R_t$=18.2 min.

c. Behavior of Nα-Acetyl-Ubiquitin (54–76) OH SEQ ID NO:4 and Tbfmoc Ubiquitin (53–76) OH SEQ ID NO:3 on PGC Nα-Acetyl-ubiquitin (54–76) OH SEQ ID NO:4 (49) was prepared from the resin-bound peptide SEQ ID NO:4 (47) by the following reactions.

Deprotection of the Fmoc group from the peptide SEQ ID NO:4 using 20% piperidine in DMF gave the peptide SEQ ID NO:4 with a free N-terminal amino group, which was then acetylated with a mixture of acetic anhydride/pyridine (1:1) (100 equiv). Removal of the peptide SEQ ID NO:4 from the resin and cleavage of the side-chain protecting groups were carried out using TFA in the presence of anisole and thioanisole as scavengers. Subsequent precipitation with ether afforded crude Nα-acetyl-ubiquitin (54–76) OH SEQ ID NO:4 (49).

Nα-(Acetyl)arginylthreonylleucylserylaspartyl-tyrosylasparagylisoleucylglutaminyllysylglutamylseryl-threonyl histidylleucylvalylleucylarginylleucylarginyl-glycylglycine, Nα-acetyl-ubiquitin (54–76) OH SEQ ID NO:4 (49)

The resin bound peptide Fmoc-ubiquitin SEQ ID NO:4 (54–76) (100 mg, 0.0151 mol) was sonicated for 30 min. in a solution of 20% piperidine in DMF (25 ml) then filtered, and finally washed well with DMF and ether. To the resin bound peptide SEQ ID NO:4 previously swollen for 30 min. in DMF (1 ml) was added acetic anhydride (143 μl, 1.51 mmol; 100 equiv.) and pyridine (122 μl, 1.51 mmol; 100 equiv.). The reaction mixture was sonicated for 1 h. The resin-bound peptide SEQ ID NO:4 was filtered and washed with DMF and ether. To the resin bound Nα-acetyl-peptide SEQ ID NO:4 was added water (50 μl), thioanisole (50 μl), anisole (50 μl) and trifluoroacetic acid (2 ml). The reaction mixture was sonicated for 2.5 h. The resin was filtered, washed with TFA (2×0.5 ml) and chloroform (2×0.5 ml). The solvent was removed in vacuo. Trituration in ether gave the product as a white precipitate which was chilled overnight, filtered and dried (43.6 mg). Purification of this peptide SEQ ID NO:4 (23.4 mg) was by preparative HPLC using the same reverse phase C-18 column with a gradient of A:B, 10 to 60% B over 16 min. and UV detection at 214 nm, to give pure Nα-acetyl-ubiquitin (54–76) OH SEQ ID NO:4 as a white solid after lyophilization (9.7 mg); amino acid analysis: $Asx_2$ 1.98, $Thr_2$ 1.82, $Ser_2$ 1.69, $Glx_2$ 2.33, $Gly_2$ 2.36, $Val_1$ 1.14, $Ile_1$ 0.91, $Leu_5$ 5.06, $Tyr_1$ 0.85, $His_1$ 1.01, $Lys_1$ 0.98, $Arg_3$ 2.87; m/z (FAB) 2712.1 ($MH^+$), HRMS 2712.49903, $C_{118}H_{200}N_{37}O_{36}$ requires 2712.49891 ( ) <1 ppm;

HPLC (A:B, A (90%) $\xrightarrow{25\text{ min.}}$ A (10%);

214 nm; C=0.2 mg/0.2 ml (A), injection: 25 μl), $R_t$=13.2 min.

The behavior of both the Nα-acetyl SEQ ID NO:4 and Tbfmoc ubiquitin SEQ ID NO:3 peptides on a PGC column was then examined.

A solution containing 5 mg of each peptide was loaded onto the column which was then eluted using different solvent mixtures. After collecting the fractions, the solvent was removed in vacuo and the residue obtained was redissolved in fresh solvent before analysis by HPLC.

The best results were obtained when a mixture of $CH_3CN/H_2O$ (1:1) was used. Under these conditions, the Nα-acetyl-peptide SEQ ID NO:4 was eluted completely by 30 ml of the mixture, whereas the Tbfmoc peptide SEQ ID NO:3 was retained.

The total chromatographic separation of these closely related peptides clearly demonstrated the efficiency of the method and its potential for the purification of peptides synthesized by solid phase methodology, provided careful attention is paid to the choice of solvents.

d. Purification of Ubiquitin (53–76) OH SEQ ID NO:3

A simple chromatographic elution on a column packed with graphitized carbon was used as the first purification step (as described in (c) above). Crude Tbfmoc ubiquitin (53–76) OH SEQ ID NO:3 (48) dissolved in a mixture of $CH_3CN/H_2O$ (1:1; 0.5% TFA) was loaded onto a column packed with PGC (50×mass of peptide). 50 ml of a mixture of the same solvent was required to completely elute the main impurities (probably Nα-acetyl ubiquitin SEQ ID NO:7 (55–76) and unreacted ubiquitin SEQ ID NO:4 (54–76)). None of the Tbfmoc peptide SEQ ID NO:4 was eluted even after flushing the column with a further 50 ml of $CH_3CN/H_2O$ (1:1). Deprotection of the Tbfmoc group was carried out using 20% piperidine in a mixture of $CH_3CN/H_2O$ (1:1) and only the desired peptide, ubiquitin (53–76) OH SEQ ID NO:3, was eluted. After removal of the solvent in vacuo, the peptide SEQ ID NO:3 was finally precipitated with ether. Subsequent purification by preparative HPLC gave pure ubiquitin (53–76) OH SEQ ID NO:3 (50) in 15% overall yield.

Glycylarginylthreonylleucylserylaspartyltyrosylaspara-
gylisoleucylglutaminyllysylglutamylserylthreonylleu-
cylhistidyl leucylvalylleucylarginylleucylarginyl-
glycylglycine (ubiquitin (53–76) OH) SEQ ID
NO:3

A solution of Tbfmoc-ubiquitin (53–76) OH SEQ ID NO:3 (30 mg; crude peptide) in a mixture of $CH_3CN/H_2O$ (1:1; 0.5% TFA; 30 ml) was sonicated for 30 min. until complete dissolution and loaded on a 5 mm diameter glass column packed with graphitized carbon (1.4 g; PGC 220–224; 150–180 μm; 100 m²/g; length after packing: 140 mm). The column was first eluted with a mixture of $CH_3CN/H_2O$ (1:1; 0.5% TFA; 50 ml). After lyophilization a residue (6.1 mg) was obtained which gave a major peak on HPLC ($R_t$=13 min., Nα-acetyl-ubiquitin SEQ ID NO:7 (55–76) or ubiquitin SEQ ID NO:4 (54–76)). The column was then eluted with a mixture of $CH_3CN/H_2O$ (1:1; 50 ml). A residue (0.4 mg) was obtained after lyophilization which was found HPLC to contain impurities. The deprotection was carried out using a 20% piperidine solution in a mixture of $CH_3CN/H_2O$ (1:1; 50 ml). The solvent was removed in vacuo to give a residue which was triturated in ether, filtered and dried (11 mg). This crude peptide SEQ ID NO:3 (11 mg) was finally purified by preparative HPLC (reverse phase C-18 column (10×250 mm); gradient (A:B), 10 to 60% B over 25 min.; detection at 214 nm) to give ubiquitin (53–76) OH SEQ ID NO:3 as a white solid after lyophilization (4.5 mg, 15%); amino acid analysis: $Asx_2$ 2.04, $Thr_2$ 1.88, $Ser_2$ 1.67, $Glx_2$ 2.27, $Gly_3$ 3.37, $Val_1$ 1.01, $Ile_1$ 0.90, $Leu_5$ 4.99, $Tyr_1$ 0.93, $His_1$ 1.01, $Lys_1$ 0.96, $Arg_3$ 2.95; m/z (FAB) 2727.8 (MH$^+$), HRMS 2727.50986, $C_{118}H_{201}N_{38}O_{36}$ requires: 2727.50981 ( ) <1 ppm;

HPLC (A:B, A (90%) $\xrightarrow{25\text{ min.}}$ A (10%);

214 nm; C=0.4 mg/0.4 ml (A), injection: 25 μl), $R_t$=12.6 min.

The identities of both Tbfmoc ubiquitin (53–76) OH SEQ ID NO:3 and ubiquitin (53–76) OH SEQ ID NO:3 peptides were established by high resolution mass spectrometry and amino acid analysis.

EXAMPLE 8

Synthesis and Purification of Ubiquitin (35–76) SEQ ID NO:5

The purification of this peptide did not pose any problems and was carried out as with the smaller ubiquitin fragment SEQ ID NO:3 (50); Tbfmoc ubiquitin (35–76) OH SEQ ID NO:5 (52) was prepared by coupling in situ Tbfmoc Gly OBt to the resin-bound peptide ubiquitin (36–76) SEQ ID NO:3 (75% yield). Following chromatography on a PGC column and preparative HPLC, the desired peptide SEQ ID NO:5 (51) could be obtained.

The authenticity of (51) was also confirmed by mass spectrometry and amino acid analysis, and its purity by analytical HPLC.

Nα-(17-Tetrabenzo(a,c,g,i)
fluorenylmethoxycarbonyl)
glycylisoleucylprolylprolylaspartylglutaminylglutaminyl
arginylleucylisoleucylphenylalanylalanylglycyllysyl-
glutaminylleucyglutamylaspartylglycylarginylthre-
onylleucylserylaspartyl tyrosylasparaglylisoleucyl-
glutaminyllysylglutamylserylthreonylleucylhistidylleu-
cylvalylleucylarginylleucylarginylglycylglycine
(Tbfmoc ubiquitin (35–76)) SEQ ID NO:5 (52)

To the Fmoc ubiquitin (36–76) resin-bound peptide SEQ ID NO:6 (109.3 mg, 7.88 μmol) in DMF (1 ml) was added acetic anhydride (14.8 μl, 157.6 μmol; 20 equiv) and pyridine (12.8 μl, 157.6 μmol; 20 equiv). The reaction mixture was sonicated for 1 h. After filtration and washing with DMF and ether, the resin bound peptide SEQ ID NO:6 was sonicated for 15 min. in a solution of 20% piperidine in DMF (25 ml). The resin bound peptide SEQ ID NO:6 was then filtered and washed well with DMF and ether. Tbfmoc GlyOH (19.6 mg, 39.4 μmol; 5 equiv) was sonicated for 30 min. in dioxan (1 ml). To this solution was added 1,3-diisopropylcarbodiimide (6.2 μl, 39.4 μmol; 5 equiv) and 1-hydroxybenzotriazole (5.3 mg, 39.4 μmol; 5 equiv). The reaction mixture was sonicated for 5 min. This solution was then added to the resin-bound peptide SEQ ID NO:6 previously swollen in dioxan (1 ml) for 1 h. The reaction mixture was sonicated for 19 h. The resin-bound peptide SEQ ID NO:5 was filtered, washed with dioxan, dichloromethane and ether, and finally dried for 48 h in a vacuum desiccator (102 mg).

Substitution Efficiency

The Tbfmoc resin bound peptide SEQ ID NO:5 (2.9 mg) was sonicated for 30 min. in a solution of 20% triethylamine in DMF (10 ml). The specific absorption at 364 nm was recorded and the following results were derived from it: A=0.65; product resin functionality in μmol/g: 50.51; resin loading/coupling percentage: 70. The coupling was then repeated under the same conditions (4 equivalents of each Tbfmoc GlyOH, 1,3-diisopropylcarbodiimide and 1-hydroxybenzotriazole; reaction time: 3.5 h). The resin bound peptide SEQ ID NO:5 was filtered, washed with dioxan, dichloromethane and ether, and finally dried overnight in a vacuum desiccator (99.5 mg).

Substitution Efficiency

A=0.265 (resin-bound peptide: 2.7 mg); product resin functionality in μmol/g: 54.26; resin loading/coupling percentage: 75.

To the resin-bound Tbfmoc-peptide SEQ ID NO:5 (96.8 mg) was added water (75 μl), thioanisole (50 μl) and TFA (2.1 ml). The reaction mixture was sonicated for 2.5 h. The resin was filtered, washed with TFA (2×0.5 ml) and $CHCl_3$ (2×1 ml), and dried (19.1 mg). The solvent was removed in vacuo to give a residue. Trituration in diethyl ether gave the crude peptide SEQ ID NO:5 as a yellow solid which was chilled overnight, washed well with ether and finally dried (49.2 mg). HPLC (A:B; A (90%)

$\xrightarrow{25\text{ min.}}$

A (10%, 214 nm; C=0.5 mg/0.5 ml (A/B (1:1)); injection 30 μl) $R_t$=19.2 min.

Glycylisoleucylprolylprolylaspartylglutaminylgluta-
minylarginylleucylisoleucylphenylalanylalanylglycyl-
lysylglutaminylleucylglutamylaspartylglycylarginyl
threonylleucylserylspartyltyrosylasparagylisoleucylglu-
taminyllysylglutamylserylthreonylleucylhistidylleu-
cylvalylleucylarginylleucylarginylglycylglycine
(ubiquitin (35–76) OH) SEQ ID NO:5 (51)

A suspension of crude Tbfmoc-ubiquitin (35–76) OH SEQ ID NO:5 (30 mg) in a mixture of $CH_3CN/H_2O$ (1:1; 0.5% TFA, 25 ml) was sonicated or 20 min. (until complete dissolution) and loaded on a 5 mm diameter glass column packed with graphitized carbon (1.5 g; PGC 220–224; 150–180 μm; 100 m²/g; active length: 15 cm). The column was first eluted with a mixture of $CH_3CN/H_2O$ (1:1; 0.5% TFA; 50 ml). After lyophilization of the eluent a residue (2 mg) was obtained which gave a broad peak on HPLC ($R_t$=13.8 min. (impurities)). The column was then eluted with a mixture of $CH_3CN/H_2O$ (1:1; 50 ml). A white solid (4.5 mg) was obtained after lyophilization which was found by HPLC also to contain impurities (broad peak, $R_t$=14.1 min.). The column was again eluted with 50 ml of a mixture of $CH_2CN/H_2O$ (1:1) and a residue (0.3 mg) was obtained after lyophilization ($R_t$=14.2 min.). The deprotection was carried out using a 20% piperidine solution in a mixture of $CH_3CN/H_2O$ (1:1; 50 ml) and was followed by an elution of the column with $CH_3CN/H_2O$ (1:1; 50 ml). The solvent was removed in vacuo to give a brown residue. Diethyl ether was added and the precipitate obtained was chilled overnight, filtered and washed well with ether, and finally dried (11.7 mg). The crude peptide SEQ ID NO:5 (24.8 mg) was finally purified by preparative HPLC (reverse phase C-18 column (10×250 nm); gradient (A:B), 0 to 60% B over 22 min.; detection at 214 nm) to give pure ubiquitin (35–76) OH as a white solid after lyophilization (4.4 mg); amino acid analysis: $Asx_4$ 3.98, $Thr_2$ 1.83, $Ser_2$ 1.75, $Glx_6$ 6.67, $Pro_2$ 1.91, $Gly_5$ 5.10, $Ala_1$ 0.96, $Val_1$ 1.01, $Ile_3$ 2.99, $Leu_7$ 7.00, $Tyr_1$ 0.94, $Phe_1$ 1.04, $His_1$ 1.11, $Lys_2$ 1.91, $Arg_4$ 3.81; m/z (FAB) 4734.2 ($MH^+$). HRMS 4734.57186, $C_{208}H_{344}N_{63}O_{63}$ requires: 4734.57161 ( ) <1 ppm;

HPLC (A:B, A (90%) $\xrightarrow{25\ min.}$ A (10%);

λ=214 nm; C=0.1 mg/0.1 ml (A); injection: 12 μl), $R_t$=3.8 min.

EXAMPLE 9

Synthesis of Tbfmoc-L-Phe OH

The free amine function of commercially available L-phenylalanine tert-butyl ester hydrochloride was initially liberated with triethylamine. The amine in 20% excess was then reacted with the mixed carbonate (41) in the presence of N,N'-dimethylaniline. After removal of the t-butyl group with TFA, compound (53) was obtained.

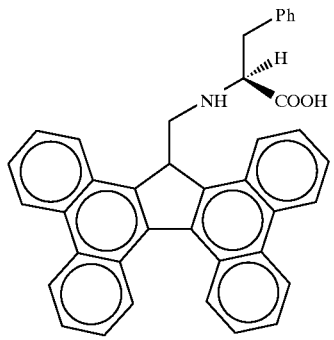
(53)

The formation of (53) may be rationalized by β elimination of the mixed carbonate (41), 1,2 addition of the amino ester onto the resulting olefin (38) and finally cleavage of the t-butyl ester.

Nα-17-Tetrabenzo(a,c,g,i)fluorenylmethyl-L-phenylalanine (Tbfm-L-Phe OH) (53)

A solution of Nα-17-tetrabenzo(a,c,g,i)fluorenylmethyl-L-phenylalanine tert-butyl ester (421.1 mg, 0.702 mmol) in trifluoroacetic acid (3.6 ml) and water (0.2 ml) was sonicated for 3.5 h at room temperature. The solvent was removed in vacuo to give a brown residue. Trituration in diethylether gave the compound (53) as a yellow solid which was chilled overnight, filtered, washed with ether, and finally dried (352.7 mg, 92%);

m.p. 178–180° C.; (Found: C, 85.2; H, 5.47; N, 2.57; $C_{39}H_{29}NO_2$ requires: C, 86.2; H, 5.37; N, 2.59%); [α]D −40.4° (C=1, TFA); t.l.c. $R_f$ (H) 0.36, $R_f$ (T) 0.62; $v_{max}$ (KBr) 3090, 3060, 3030 (CH stretching, aryl), 1620 (COO⊖), 1500 (aromatic rings), 1240, 1190, 1040 (CO stretching), 750, 725, 700 (CH out-of-plane deformation) $cm^{-1}$; $\lambda^{max}$ 384 (18868), 369 (21267), 304 (52447), 292 (41894), 264 (78991), 255 (86346) nm; δC (TFA, 50 MHz) 169.5 (CO, acid), 137.9, 136.9, 136.1, 134.2, 131.8, 131.4, 130.5, 129.8, 126.3, 126.1, 125.8 (quaternary aromatic C's) 128.7, 127.9, 127.2, 127.0, 126.8, 124.8, 123.44, 123.34, 123.29, 122.2 (aromatic CH's), 62.2 (α CH), 50.9 ($CH_2$), 43.2 (CH), 34.2 (β $CH_2$); m/z (FAB) 544 ($MH^{30}$ ), 379. HRMS 544.22762, $C_{39}H_{30}NO_2$ requires: 544.22764 ( ) <1 ppm.

As the acetate of glycine was successful in the synthesis of Tbfmoc Gly OH, this method is also useful in this case; thus the acetate salt of L-phenylalanine tert-butyl ester was prepared.

The hydrochloride salt of the amino acid ester was neutralized with triethylamine and the precipitated $Et_3N.HCl$ generated was filtered off. Following removal of the solvent, the residue obtained was redissolved in acetic acid before lyophilization. Subsequent reaction with the mixed carbonate (41) in the presence of two equivalents of N,N'-dimethylaniline afforded Tbfmoc-L-Phe O'Bu (54) in 46% yield after purification by flash chromatography and recrystallization. Final cleavage of the '-butyl ester using a mixture of $TFA/H_2O$ (95:5) gave Tbfmoc-L-Phe OH (55) in excellent yield.

Nα-17-Tetrabenzo(a,c,g,i)fluorenylmethoxycarbonyl-L-phenylalanine tert-butyl Ester (Tbfmoc Phe O'-Bu) (54)

To a suspension of L-phenylalanine tert-butyl ester hydrochloride (126.7 mg, 0.491 mmol) in ethyl acetate (6 ml) was added triethylamine (68.5 μl, 0.491 mmol). The reaction mixture was stirred for 2.5 h at room temperature. The precipitated triethylamine hydrochloride was filtered off, washed with ethyl acetate (2×0.5 ml) and dried (65.3 mg, 97%). The filtrate was evaporated to give a residue which was redissolved in acetic acid. Following lyophilization the acetate salt was obtained as a white solid (83.9 mg, 61%).

To a solution of 17-tetrabenzo(a,c,g,i)fluorenylmethyl-para-nitrophenyl carbonate (139.4 mg, 0.248 mmol) and L-phenylalanine tert-butyl ester acetate (83.9 mg, 0.298 mmol; 1.2 equiv) in dichloromethane (5 ml) was added N,N'-dimethylaniline (63 μl, 0.497 mmol; 2 equiv). The reaction mixture was stirred at room temperature under nitrogen for 120 h. After addition of water (10 ml) and acidification with $KHSO_4$ (2M) to pH=1, the reaction mixture was extracted with dichloromethane (3×20 ml). The combined organic phases were washed with water (2×15 ml) to pH 6–7 and dried over $MgSO_4$. After filtration the solvent was evaporated under reduced pressure to give an orange oil. After purification by flash chromatography using toluene as the eluent, the fractions containing material of $R_f$=0.04 were evaporated to give a yellow solid. Recrystallization from ether/petrol (b.p. 40–60° C.) gave compound (54) as a pale yellow solid which was filtered, washed with petrol and finally dried (73.9 mg, 46%);

m.p. 158–162° C. (dec); t.l.c. $R_f$(C) 0.04, $R_f$(H) 0.84; $\nu_{max}$ (KBr) 3280 (NH stretching), 3060, 3030 (CH stretching, aryl), 2980, 2930 (CH stretching, alkyl), 1735 (CO, ester), 1715 (CO, urethane), 1680 (amide I), 1610 (aromatic rings), 1545 (amide II), 1500 (aromatic rings.) 1440 (CH deformations, alkyl), 1390, 1370 ($CH_3$, symmetrical deformations), 1290, 1255, 1220, 1155, 1050 (CO stretching), 850, 750, 720, 700 (out-of-plane CHdeformation) $cm^{-1}$; m/z (FAB) 643 ($M^+$), 379. HRMS 643.27225, $C_{44}H_{37}NO_4$ requires: 643.27224 ( ) <1 ppm.

Nα-17-Tetrabenzo(a,c,g,i) fluorenylmethoxycarbonyl-L-phenylalanine (Tbfmoc-L-Phe OH) (55)

A solution of Nα-17-tetrabenzo(a,c,g,i) fluorenylmethoxycarbonyl-L-phenylalanine tert-butyl ester (68.2 mg, 0.106 mmol) in trifluoroacetic acid (950 μl) and water (50 μl) was sonicated for 2.5 h. The solvent was removed in vacuo to give a purple residue. A mixture of diethyl ether and petrol b.p. 40–60° C. (1:1) was added. The precipitate obtained was chilled overnight, filtered, washed with petrol and finally dried in a vacuum desiccator over $P_2O_5$ to give compound (55) (57.6 mg, 93);

m.p. 137–140° C.; [d]D −50.8 (C=0.25, $CH_2Cl_2$); t.l.c.: $R^f$(H) 0.43, $R_f$(I) 0.89; $\nu_{max}$ (KBr) 3410 (NH stretching), 3060, 3030 (CH stretching, aryl), 2960, 2860 (CH stretching, alkyl), 1715 (CO, acid and urethane), 1610, 1500 (aromatic rings), 1435, 1420 (CH deformations, alkyl), 1340 (OH bending), 1215, 1050 (CO stretching), 750, 730, 700 (out-of-plane CH deformation) $cm^{-1}$; $\nu_{max}$ 384 (15794), 368 (16896), 302 (39670), 290 (32324), 262 (59505), 254 (64647) nm; δH ($CDCl_3$, 200 MHz) 8.80–8.58 (6H, m, aromatic), 8.30–8.19 (2H, m, aromatic), 7.65–7.54 (8H, m, aromatic), 7.19–7.07 (5H, m, aromatic (Phe)), 5.13 (1H, apparent t, CH), 4.98 (1H, d, $_3$J=8.4 Hz, NH), 4.79–4.64 (2H, m, $H_a$ ($CH_2$) and αCH (Phe)), 4.30–4.24 (1H, m, $H_b$ ($CH_2$)), 3.08 (2H, m, β $CH_2$ (Phe)); δc ($CDCl_3$, 90 MHz), 175.8 (CO, acid), 155.8 (CO, urethane), 142.6, 141.0, 136.8, 136.5, 135.3, 131.5, 130.3, 130.1 (quaternary aromatic C's), 129.0, 128.6, 127.4, 127.3, 127.1, 126.8, 126.6, 125.9, 125.7, 125.5, 125.1, 124.9, 124.8, 123.4, 123.1, 123.0 (aromatic CH's), 69.2 ($CH_2$), 54.4 (α CH), 47.4 (CH), 37.4 (β $CH_2$); m/z (FAB) 587 ($M^+$), 379. HRMS 588.21744, $C_{40}H_{30}NO_4$ requires: 588.21747 ( ) <1 ppm.

What is claimed is:

1. A process for synthesis or separation of a mixture of compounds, comprising the steps of:
   a) protecting at least one group in at least one compound in a mixture of compounds to be separated with a protective group having the formula (I):

Ar—L—  (I)

wherein
   Ar represents a substantially planar fused ring system containing at least 4 aromatic rings; and
   L represents a group containing at least one carbon atom which is capable of bonding to a group to be protected; and
   b) passing the mixture of compounds through a chamber filled with a graphite material.

2. A process for synthesis or separation of a mixture of compounds, comprising the steps of:
   a) protecting at least one group in at least one compound selected from peptide, a nucleoside and a nucleotide, in a mixture of compounds to be separated, with a protective group having the formula (I):

Ar—L  (I)

wherein
   Ar represents a substantially planar fused ring system containing at least 4 aromatic rings; and
   L represents a group containing at least one carbon atom which is capable of bonding to a group to be protected; and
   b) passing the mixture of compounds through a chamber filled with a graphite material.

3. A process for synthesis or separation of a mixture of compounds, comprising the steps of:
   a) protecting at least one group in at least one compound in a mixture of compounds to be separated with a protective group having the formula (I):

Ar—L  (I)

wherein
   Ar represents a substantially planar fused ring system containing at least 4 aromatic rings; and
   L represents a group containing at least one carbon atom which is capable of bonding to a group to be protected;
   b) passing the mixture of compounds through a chamber filled with a graphite material; and
   c) removing the protective group from said at least one group in said at least one compound.

4. A process according to claim 3 wherein the protective group has the formula (IA):

Ar—$(CH_2)_n$—CRR'—  (IA)

wherein
   R and R' are each hydrogen, alkyl, aryl, aralkyl or cycloalkyl; and
   n is an integer of from 0 to 5,
   and is removed by acidolysis.

5. A process according to claim 3 wherein the protective group has the formula (IB) or (IC):

Ar—$(CH_2)_n$—$C(CY_m)(R)$—  (IB)

Ar—$(CH_2)_n$—$(CF_2)_m$—$C(R)_2$—  (IC)

wherein
   R is hydrogen, alkyl, aryl, aralkyl or cycloalkyl;
   Y is halogen;
   n is an integer of from 0 to 5; and
   m is an integer of from 1 to 8,
   and is removed by treatment with zinc and acetic acid.

6. A process according to claim 3 wherein the protective group has the formula (ID):

Ar—$(CH_2)_n$—CH=C(R)—CHR'—  (ID)

wherein
   R and R' are each hydrogen, alkyl, aryl, aralkyl or cycloalkyl; and
   n is an integer of from 0 to 5,
   and is removed by treating said at least one group in at least one compound with a catalyst comprising a Group VIII element complexed with a water-soluble coordinating agent in an aqueous phase.

7. A process according to claim 3 wherein the protective group has the formula (ID):

Ar—$(CH_2)_n$—CH=C(R)—CHR'—  (ID)

wherein
   R and R' each hydrogen, alkyl, aryl, aralkyl or cycloalkyl; and
   n is an integer of from 0 from to 5,
   and is removed by hydrogenation over a hydrogenation catalyst.

8. A process for synthesis or separation of a mixture of compounds, comprising the steps of:
   a) protecting at least one group in at least one compound in a mixture of compounds to be separated with a protective group having the formula (I):

Ar—L  (I)

wherein
   Ar represents a substantially planar fused ring system containing at least 6 aromatic rings; and
   L represents a group containing at least one carbon atom which is capable of bonding to a group to be protected; and b) passing the mixture of compounds through a chamber filled with a graphite material.

9. A process according to claim 8 wherein the aromatic rings are hexagonal.

10. A process for synthesis or separation of a mixture of compounds, comprising the steps of:
   a) protecting at least one group in at least one compound in a mixture of compounds to be separated with a protective group having the formula (I):

Ar—L  (I)

wherein
   Ar represents a substantially planar fused ring system containing at least 4 hexagonal aromatic rings; and
   L represents a group containing at least one carbon atom which is capable of bonding to a group to be protected; and
   b) passing the mixture of compounds through a chamber filled with a graphite material.

11. A process for synthesis or separation of a mixture of compounds, comprising the steps of:
   a) protecting at least one group in at least one compound in a mixture of compounds to be separated with a protective group having the formula (I):

Ar—L  (I)

wherein
   Ar represents a substantially planar fused ring system containing at least 4 aromatic rings and wherein Ar contains no heteroatom; and
   L represents a group containing at least one carbon atom which is capable of bonding to a group to be protected; and
   b) passing the mixture of compounds through a chamber filled with a graphite material.

12. A process for synthesis or separation of a mixture of compounds, comprising the steps of:
   a) protecting at least one group in at least one compound in a mixture of compounds to be separated with a protective group having the formula (II):

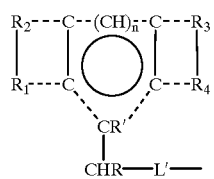   (II)

wherein
   the protective group is a substantially planar fused ring system containing at least 4 aromatic rings;
   n is an integer of 0 or 1;
   O means that the surrounding ring is aromatic when n is 1 and non-aromatic when n is 0;
   $R_1$ and $R_2$ together and $R_3$ and $R_4$ together form a fused aromatic ring system together with the carbon atoms to which they are attached;
   R and R' are each an alkyl group or hydrogen, provided that when n is 1, R' is absent; and
   L' represents a direct bond or a group capable of bonding to a group to be protected; and
   b) passing the mixture of compounds through a chamber filled with a graphite material.

13. A process according to claim 12 wherein L' is —CO—, —O—CO—, —S—, —O—, —(CH$_2$)$_m$—O—, wherein m is from 1 to 6, or a direct bond.

14. A process for synthesis or separation of a mixture of compounds, comprising the steps of:
   a) protecting at least one group in at least one compound in a mixture of compounds to be separated with a protective group having the formula (III):

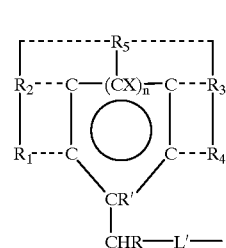   (III)

wherein
   n is an integer of 0 or 1;
   O means that the surrounding ring is aromatic when n is 1 and non-aromatic when n is 0;
   $R_1$ and $R_2$ together and $R_3$ and $R_4$ together form a fused aromatic ring system together with the carbon atoms to which they are attached;
   R and R' are each an alkyl group or hydrogen, provided that when n is 1, R' is absent;
   L' represents a direct bond or a group capable of bonding to a group to be protected;
   $R_5$ is a group which, together with the atoms to which it is attached, forms one or more supplementary rings; and
   X represents a bond to $R_5$ or a hydrogen atom; and
   b) passing the mixture of compounds through a chamber filled with a graphite material.

15. A process according to claim 14 wherein L' is —CO—, —O—CO—, —S—, —O—, —(CH$_2$)$_m$—O—, wherein m is from 1 to 6, or a direct bond.

* * * * *

UNITED STATES PATENT AND TRADEMARK OFFICE
CERTIFICATE OF CORRECTION

PATENT NO. : 6,359,113 B1
DATED : March 19, 2002
INVENTOR(S) : Robert Ramage et al.

It is certified that error appears in the above-identified patent and that said Letters Patent is hereby corrected as shown below:

Column 37,
Line 32, "from peptide" should read -- from a peptide --.

Column 38,
Line 49, "R' each" should read -- R' are each --.
Line 51, "0 from to 5" should read -- 0 to 5 --.

Signed and Sealed this

Fifteenth Day of October, 2002

Attest:

Attesting Officer

JAMES E. ROGAN
Director of the United States Patent and Trademark Office